(12) United States Patent
You

(10) Patent No.: US 11,919,237 B2
(45) Date of Patent: Mar. 5, 2024

(54) 3D BIOPRINTER

(71) Applicant: ROKIT HEALTHCARE INC., Seoul (KR)

(72) Inventor: Seok Hwan You, Seoul (KR)

(73) Assignee: ROKIT HEALTHCARE INC., Seoul (KR)

( * ) Notice: Subject to any disclaimer, the term of this patent is extended or adjusted under 35 U.S.C. 154(b) by 227 days.

(21) Appl. No.: 17/424,438

(22) PCT Filed: Oct. 29, 2019

(86) PCT No.: PCT/KR2019/014331
§ 371 (c)(1),
(2) Date: Jul. 20, 2021

(87) PCT Pub. No.: WO2021/071006
PCT Pub. Date: Apr. 15, 2021

(65) Prior Publication Data
US 2022/0088875 A1 Mar. 24, 2022

(30) Foreign Application Priority Data

Oct. 8, 2019 (KR) .................. 10-2019-0124572

(51) Int. Cl.
*B29C 64/371* (2017.01)
*B29C 64/241* (2017.01)
(Continued)

(52) U.S. Cl.
CPC .......... *B29C 64/371* (2017.08); *B29C 64/241* (2017.08); *B29C 64/295* (2017.08);
(Continued)

(58) Field of Classification Search
CPC ... B29C 64/106; B29C 64/124; B29C 64/227; B29C 64/241; B29C 64/295;
(Continued)

(56) References Cited

U.S. PATENT DOCUMENTS

2004/0104515 A1* 6/2004 Swanson ................. B29C 64/40
264/497
2017/0057173 A1* 3/2017 van der Zalm ........ B33Y 50/02
(Continued)

FOREIGN PATENT DOCUMENTS

CN 104758085 B 11/2016
CN 106222085 A * 12/2016 ............. B33Y 10/00
(Continued)

OTHER PUBLICATIONS

Yoshimura, JP6535785, machine translation Japanese to English, Jun. 26, 2019 (Year: 2019).*
(Continued)

*Primary Examiner* — Joseph S Del Sole
*Assistant Examiner* — Lawrence D. Hohenbrink, Jr.
(74) *Attorney, Agent, or Firm* — Osha Bergman Watanabe & Burton LLP

(57) ABSTRACT

A three-dimensional (3D) bioprinter includes: a case, a printing chamber surrounded by wall surfaces, a moving unit including a horizontal moving unit installed in a space under a bottom surface of the printing chamber and a vertical moving unit installed outside a side surface of the printing chamber, a bed disposed above a bottom surface opening of the bottom surface of the printing chamber, a first bellows which covers a space between the bed and an inner circumferential surface of the bottom surface opening, a first print module provided in the printing chamber and installed to be vertically movable by the vertical moving unit in a Z-axis direction, a second print module provided at one side of the first print module in the printing chamber and installed to be vertically movable by the vertical moving unit in the Z-axis direction, and a controller.

17 Claims, 16 Drawing Sheets

(51) Int. Cl.
  *B29C 64/295*    (2017.01)
  *B29C 64/321*    (2017.01)
  *B29C 64/393*    (2017.01)
  *B33Y 30/00*    (2015.01)
  *B33Y 70/00*    (2020.01)
  *G01D 5/14*    (2006.01)
  *B29C 64/106*    (2017.01)
  *B29C 64/124*    (2017.01)
  *B29C 64/227*    (2017.01)
  *B29K 105/00*    (2006.01)
  *B33Y 10/00*    (2015.01)
  *B33Y 40/00*    (2020.01)
  *B33Y 40/20*    (2020.01)
  *B33Y 50/02*    (2015.01)
  *C12M 1/26*    (2006.01)
  *C12M 1/36*    (2006.01)
  *C12M 3/00*    (2006.01)

(52) U.S. Cl.
  CPC .......... B29C 64/321 (2017.08); B29C 64/393 (2017.08); B33Y 30/00 (2014.12); B33Y 70/00 (2014.12); G01D 5/145 (2013.01); *B29C 64/106* (2017.08); *B29C 64/124* (2017.08); *B29C 64/227* (2017.08); *B29K 2105/0035* (2013.01); *B29K 2105/0058* (2013.01); *B33Y 10/00* (2014.12); *B33Y 40/00* (2014.12); *B33Y 40/20* (2020.01); *B33Y 50/02* (2014.12); *C12M 21/08* (2013.01); *C12M 33/00* (2013.01); *C12M 41/48* (2013.01)

(58) Field of Classification Search
  CPC ... B29C 64/321; B29C 64/371; B29C 64/393; B33Y 10/00; B33Y 30/00; B33Y 40/00; B33Y 40/20; B33Y 50/02; B33Y 70/00; G01D 5/145; C12M 21/08; C12M 33/00; C12M 41/48; B29K 2105/0035; B29K 2105/0058
  USPC .................................. 264/401, 494; 425/375
  See application file for complete search history.

(56) References Cited

U.S. PATENT DOCUMENTS

| | | | | |
|---|---|---|---|---|
| 2018/0099453 | A1* | 4/2018 | Cambron | B33Y 30/00 |
| 2018/0281280 | A1* | 10/2018 | Solorzano | C12N 5/0062 |
| 2019/0232558 | A1* | 8/2019 | You | B33Y 40/00 |

FOREIGN PATENT DOCUMENTS

| | | | | |
|---|---|---|---|---|
| CN | 106222085 A | | 12/2016 | |
| JP | 2018145526 A | | 9/2018 | |
| JP | 6535785 B2 | * | 6/2019 | ............. B22F 10/00 |
| KR | 101828345 | * | 3/2018 | ........... B29C 64/106 |
| KR | 101828345 B1 | | 3/2018 | |
| WO | 2015120538 A1 | | 8/2015 | |

OTHER PUBLICATIONS

He et al., CN106222085A, machine translation Chinese to English, Dec. 14, 2016 (Year: 2016).*
International Search Report issued in International Application No. PCT/KR2019/014331 dated Jul. 8, 2020 (2 pages).
Written Opinion issued in International Application No. PCT/KR2019/014331 dated Jul. 8, 2020 (5 pages).

* cited by examiner

[Fig. 1]
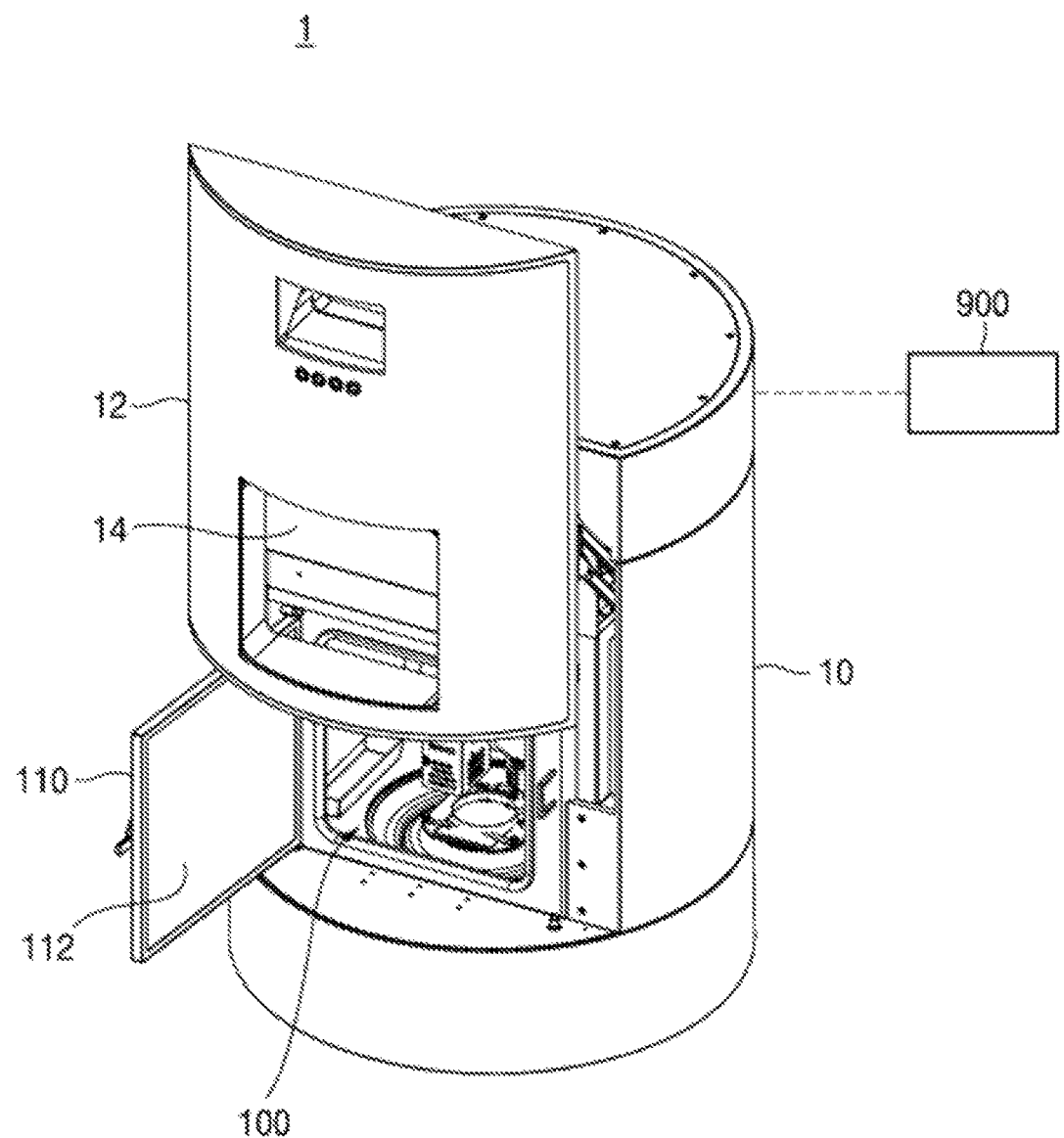

[Fig. 2]
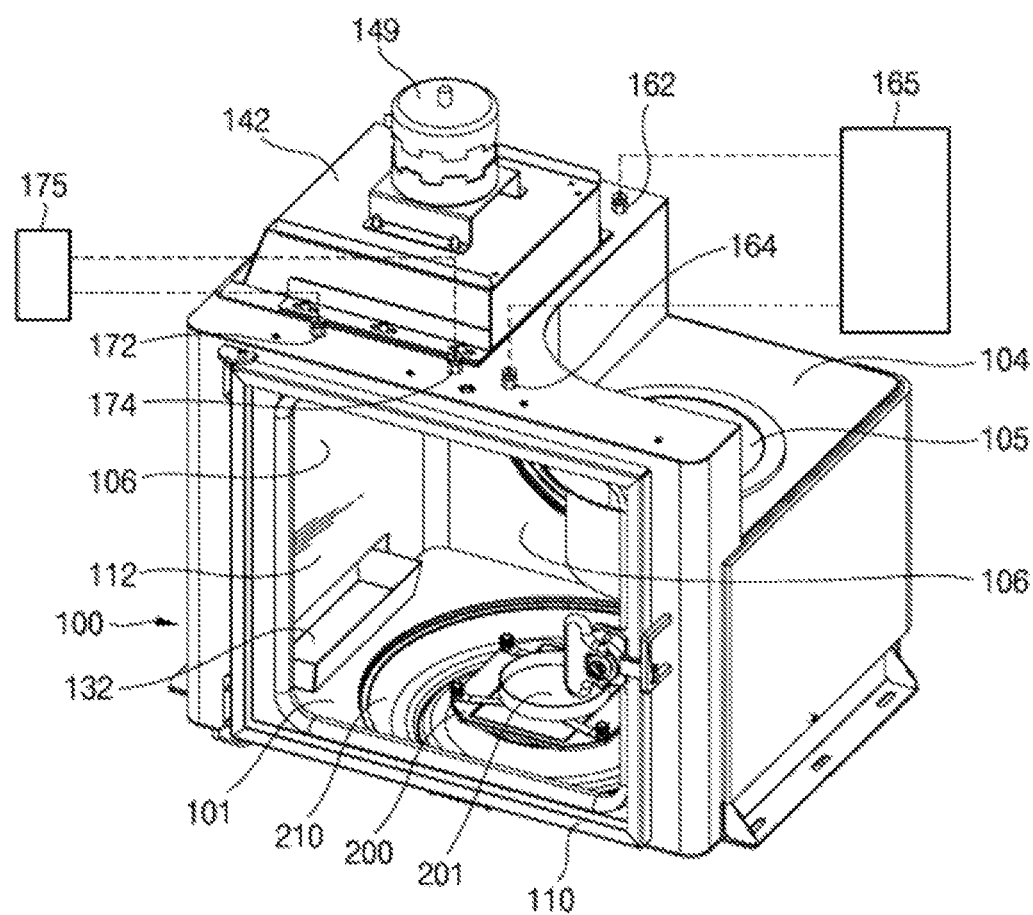

[Fig. 3]
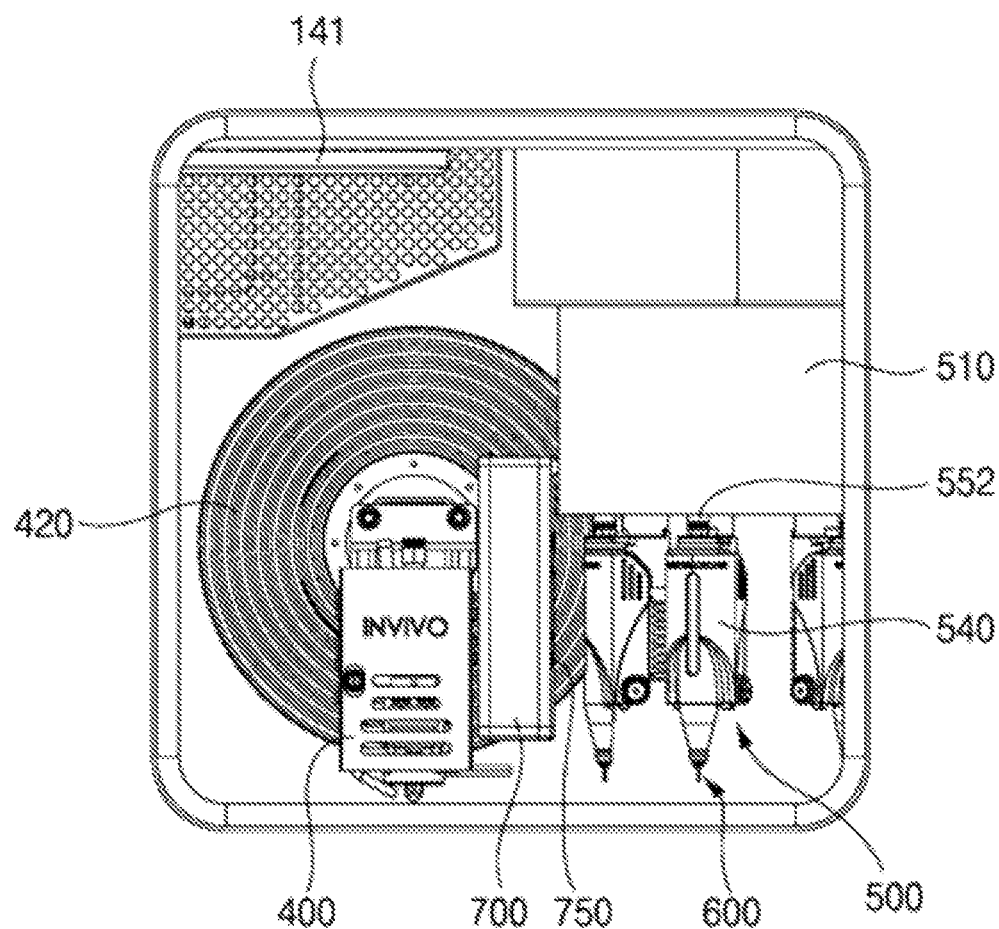

[Fig. 4]
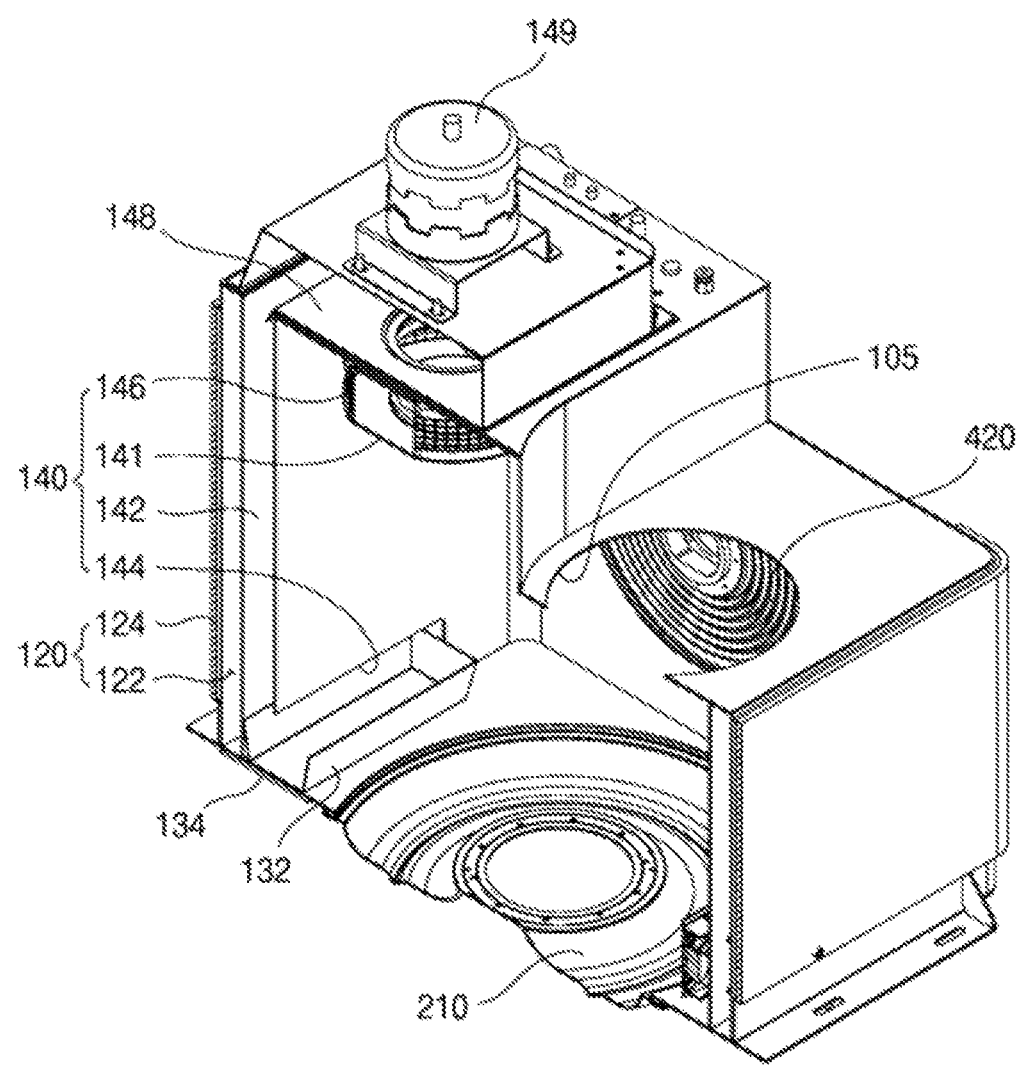

[Fig. 5]
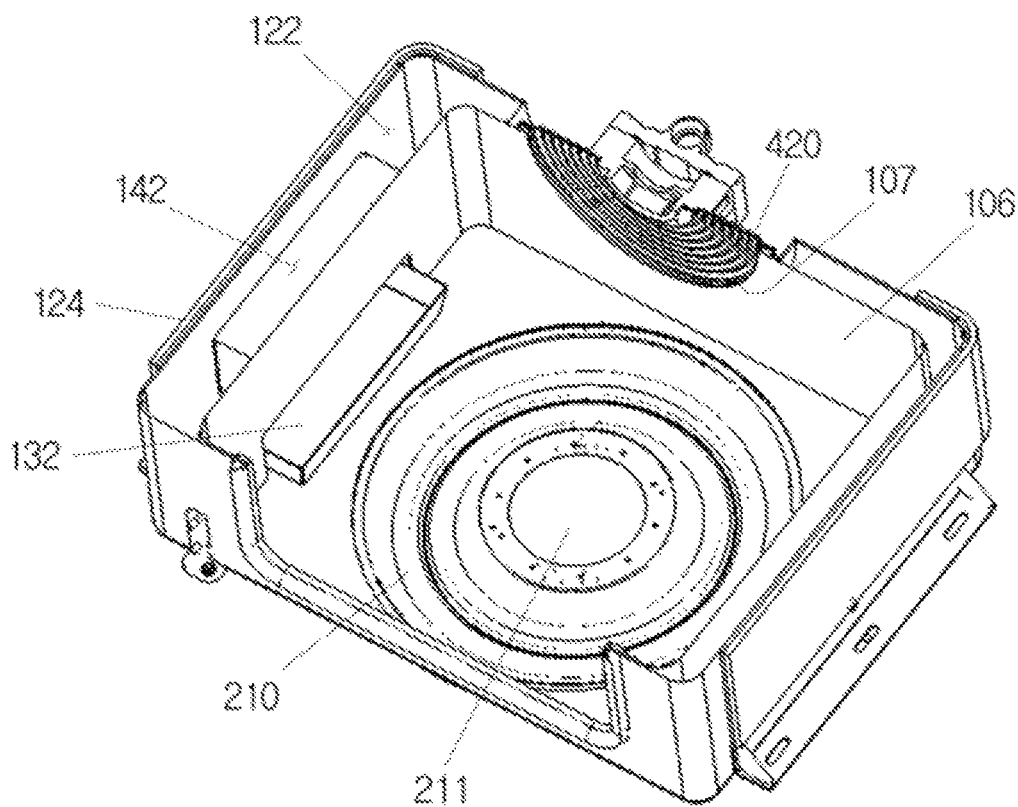

[Fig. 6]
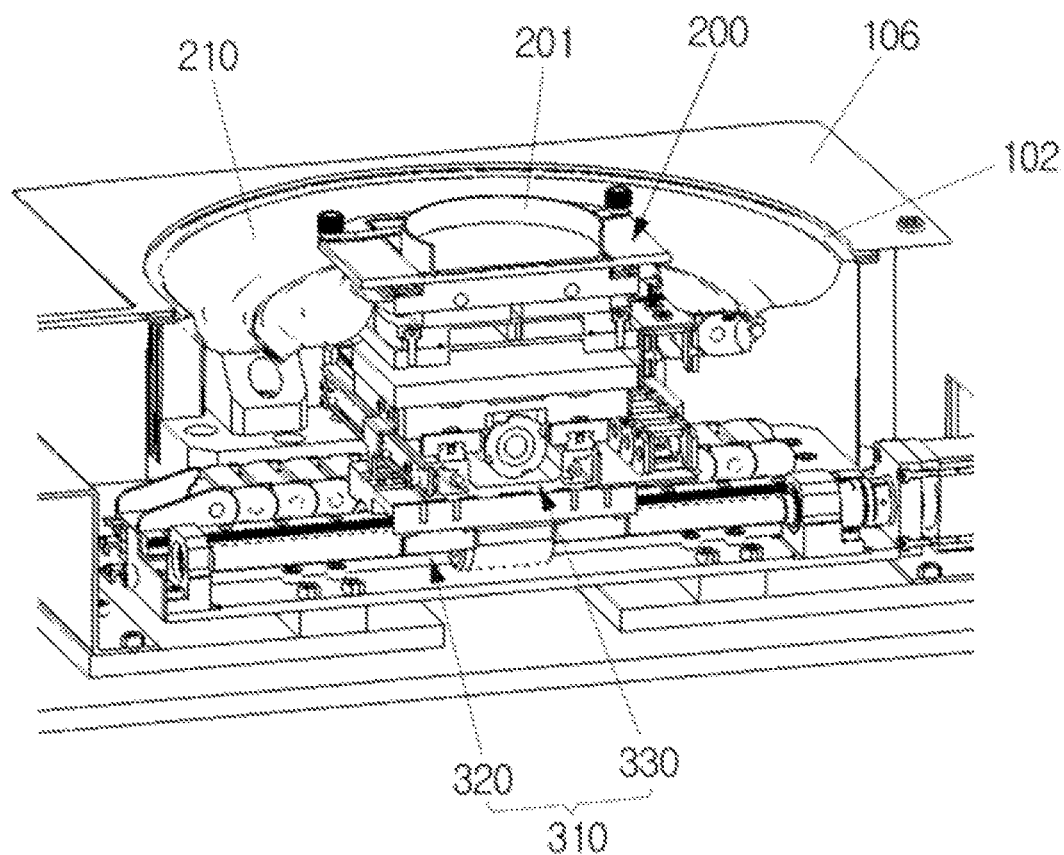

[Fig. 7]
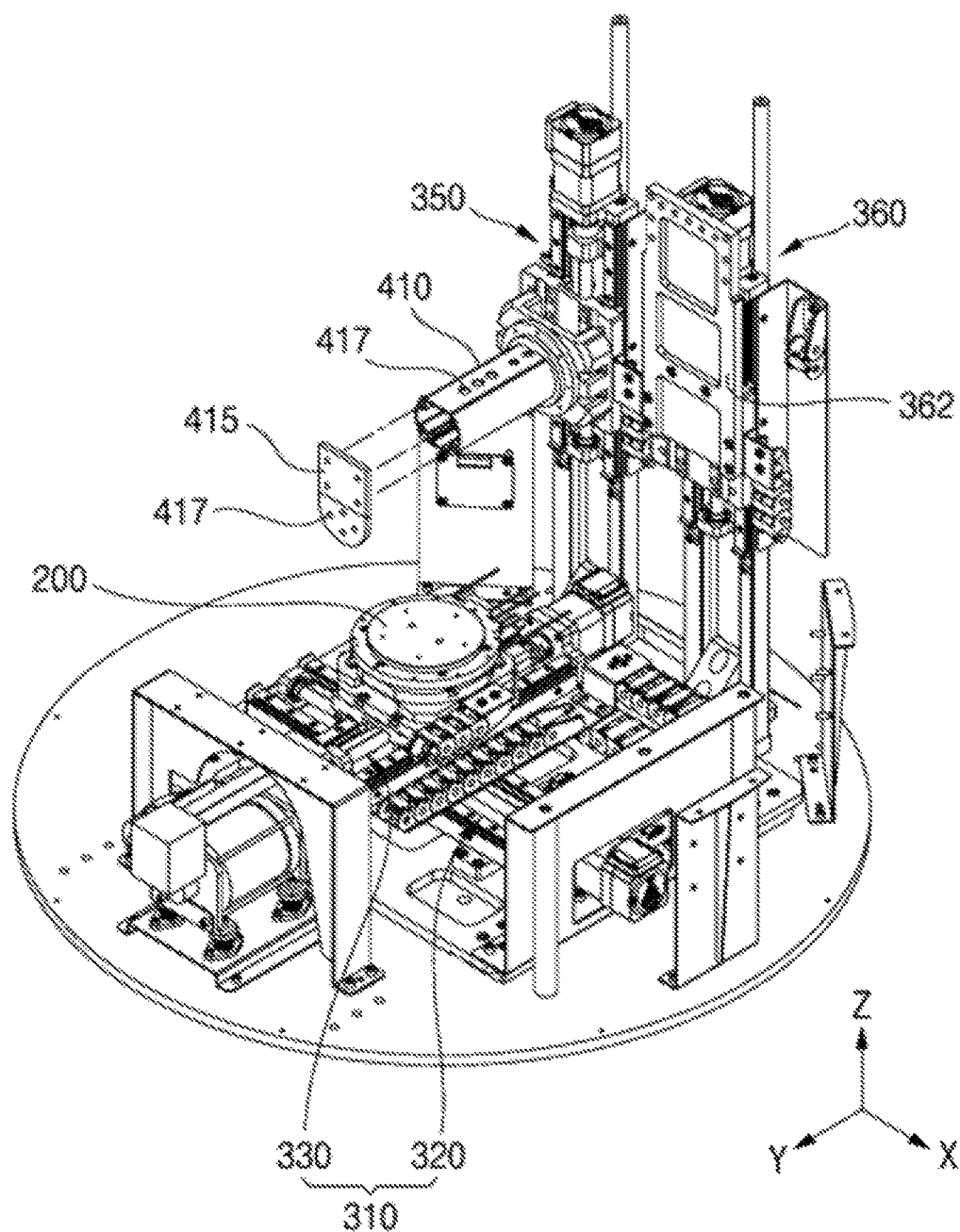

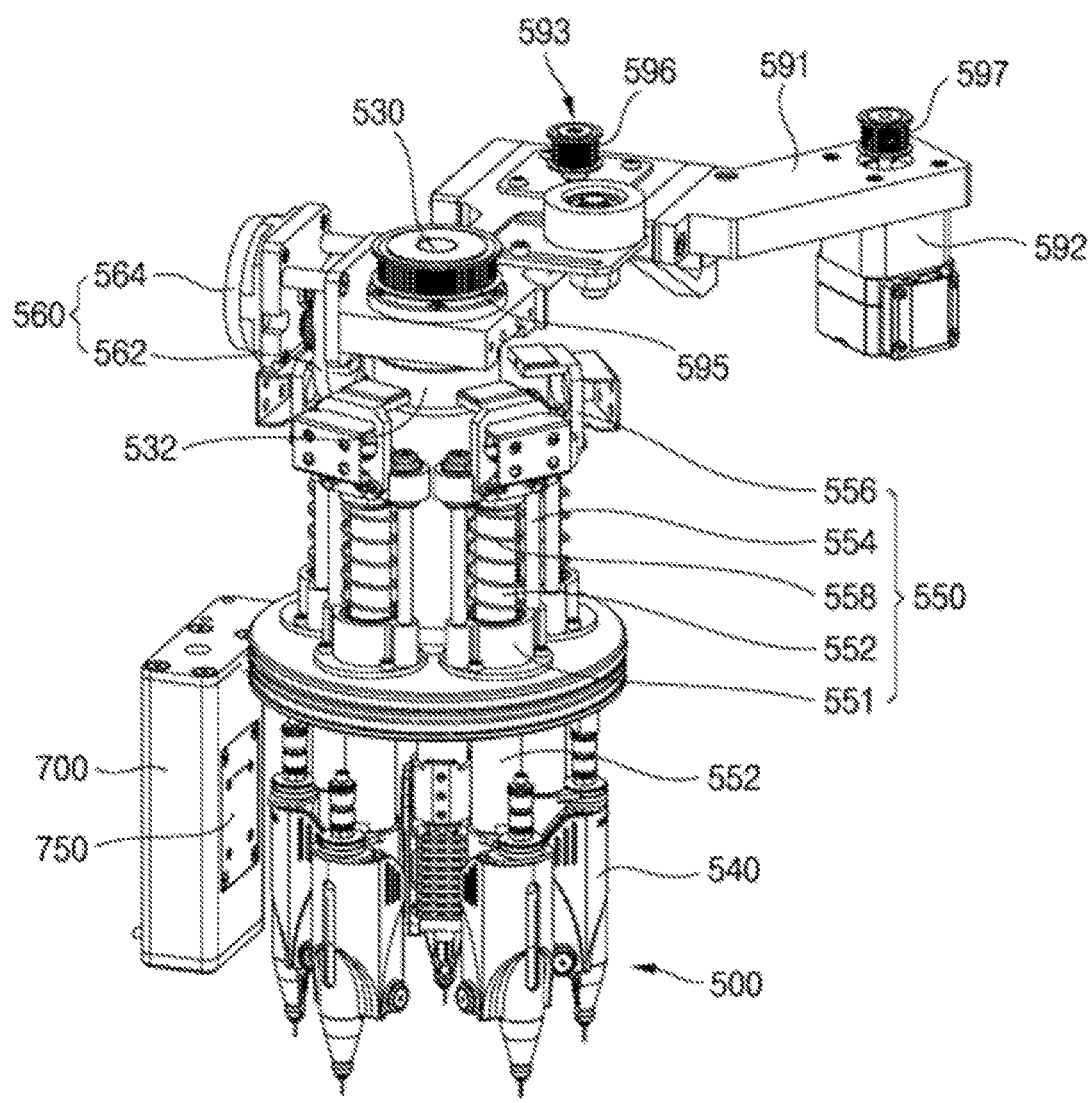
[Fig. 8]

[Fig. 9]
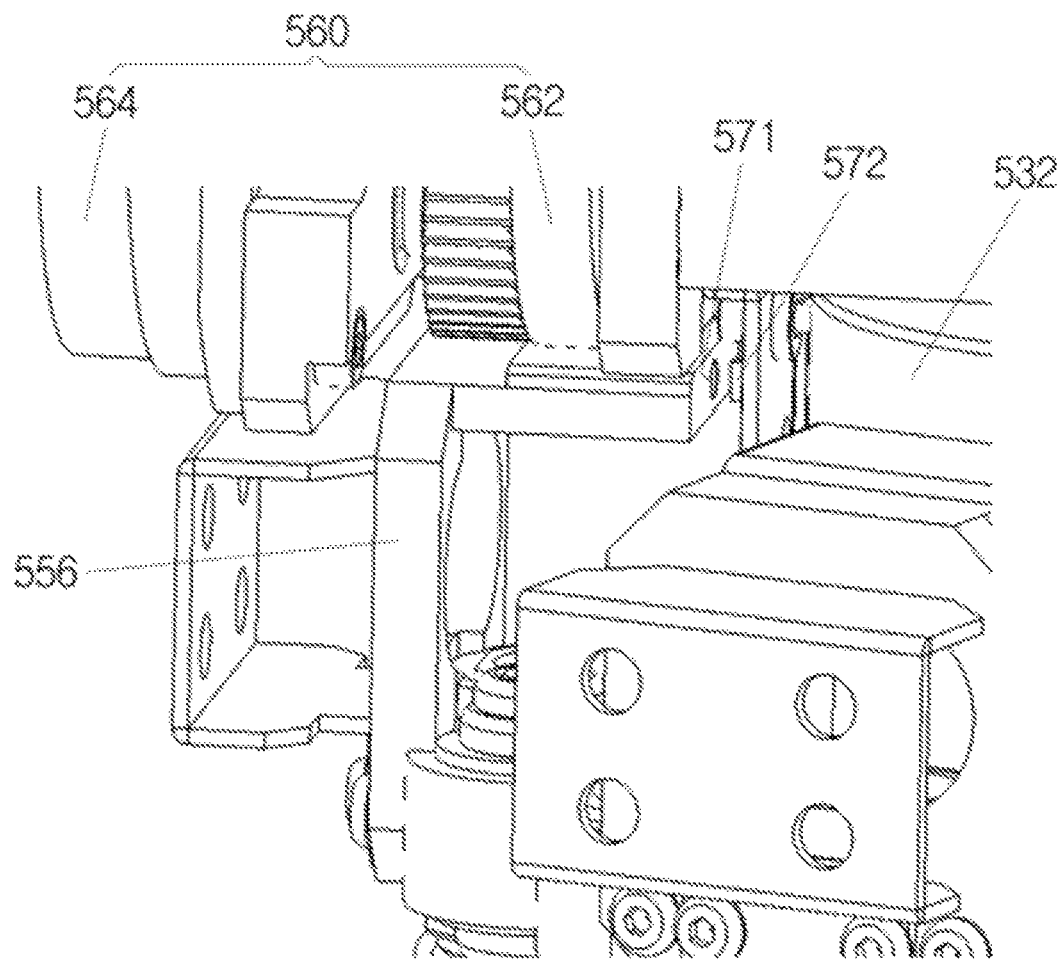

[Fig. 10]
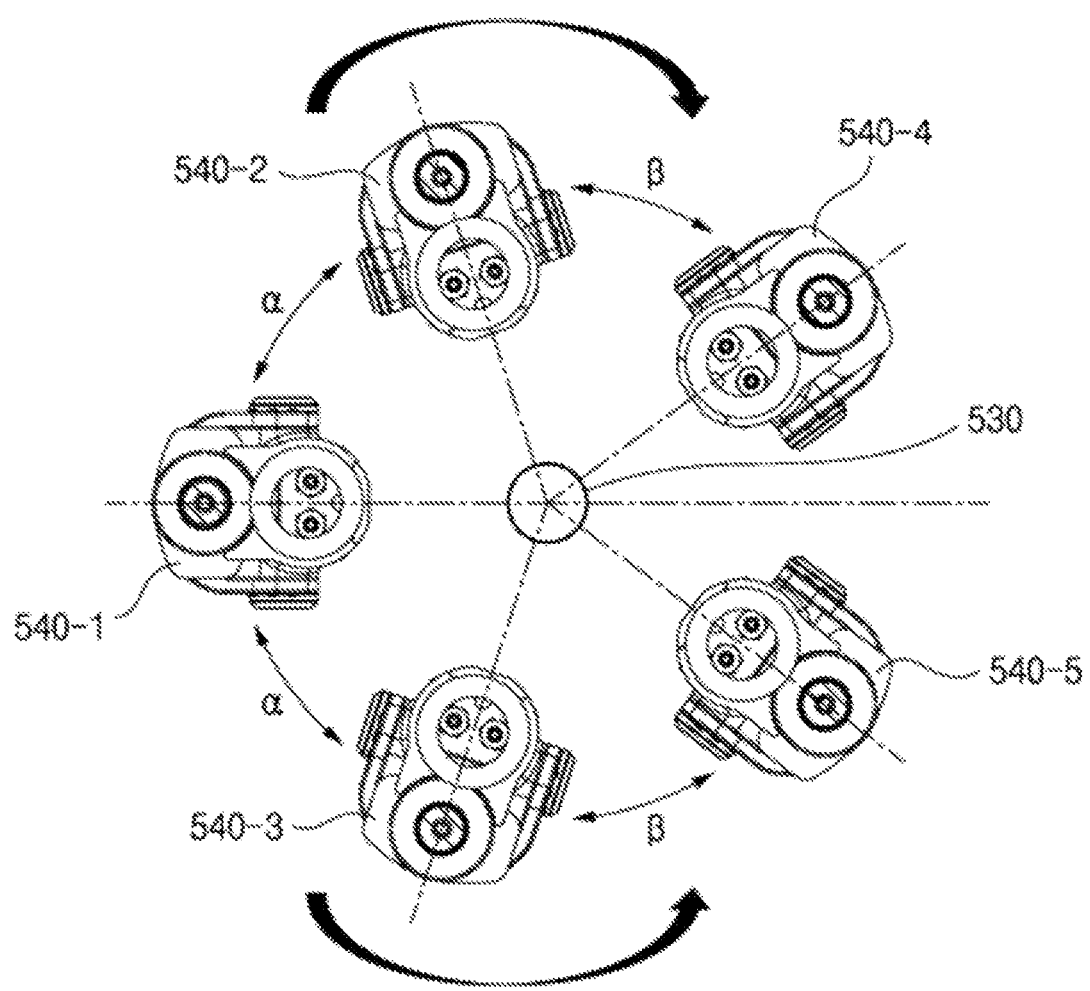

[Fig. 11]
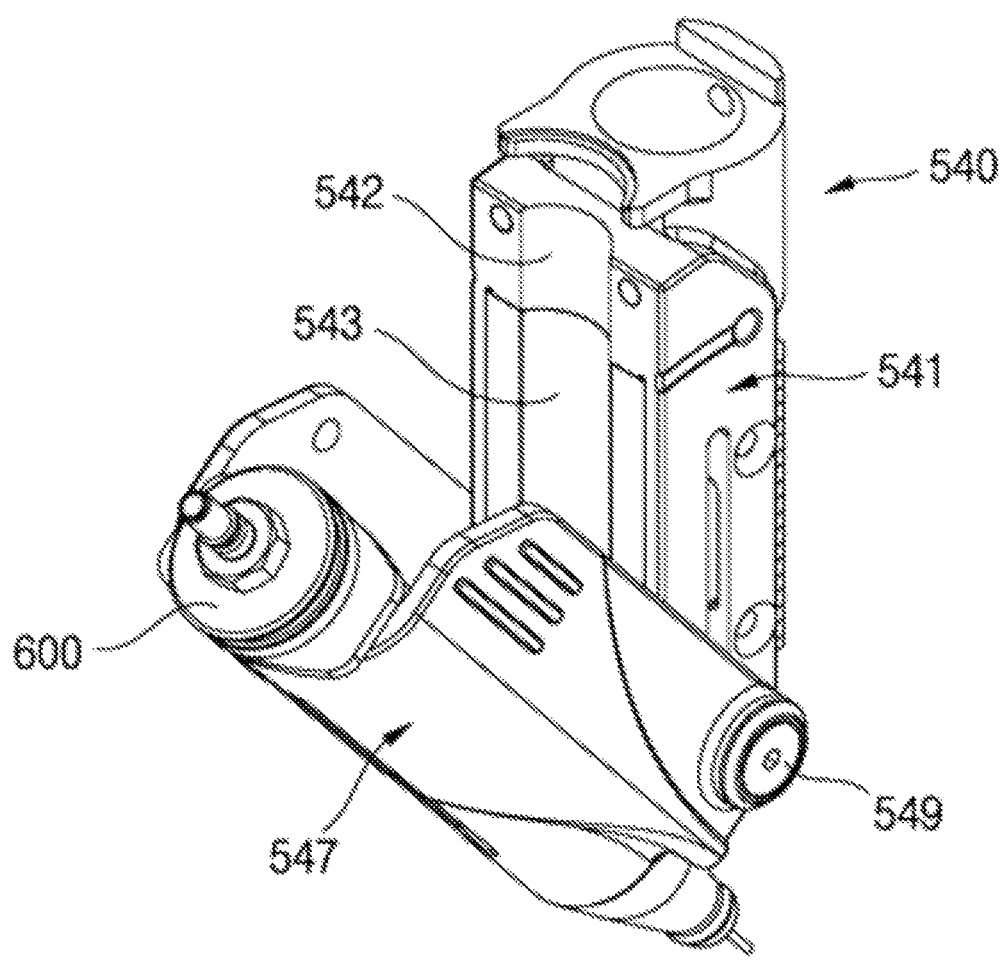

[Fig. 12]
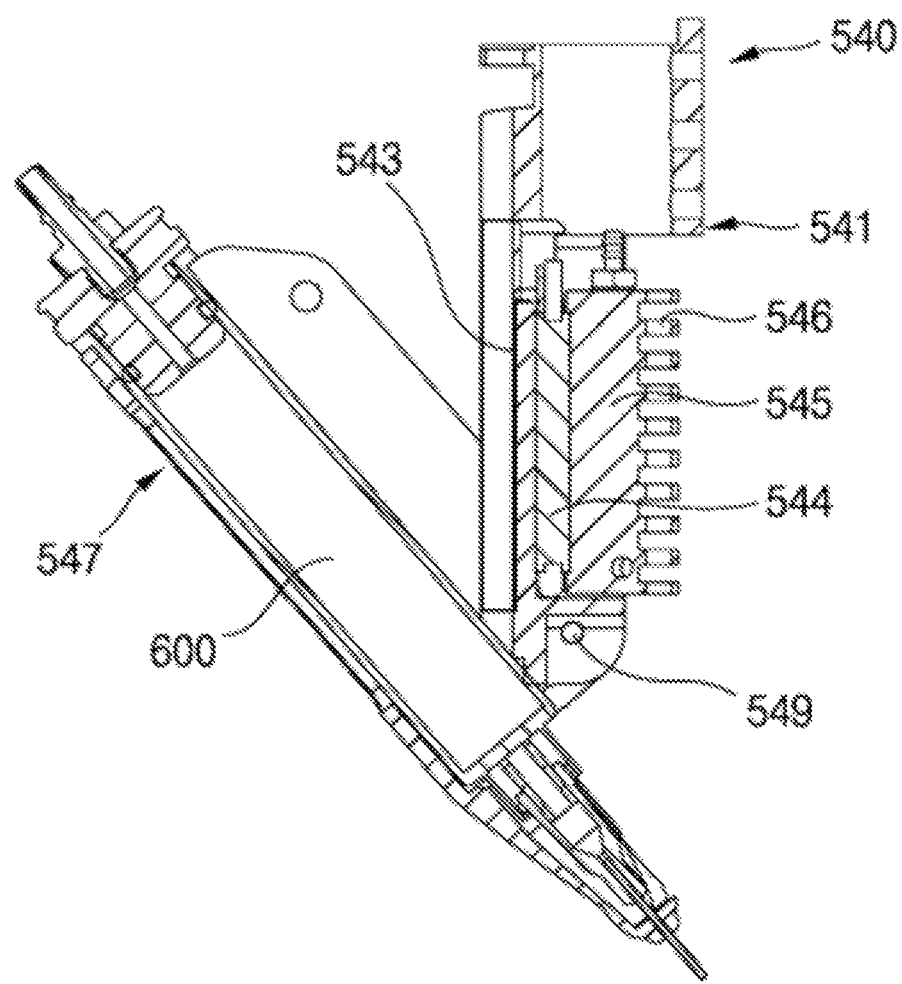

[Fig. 13]
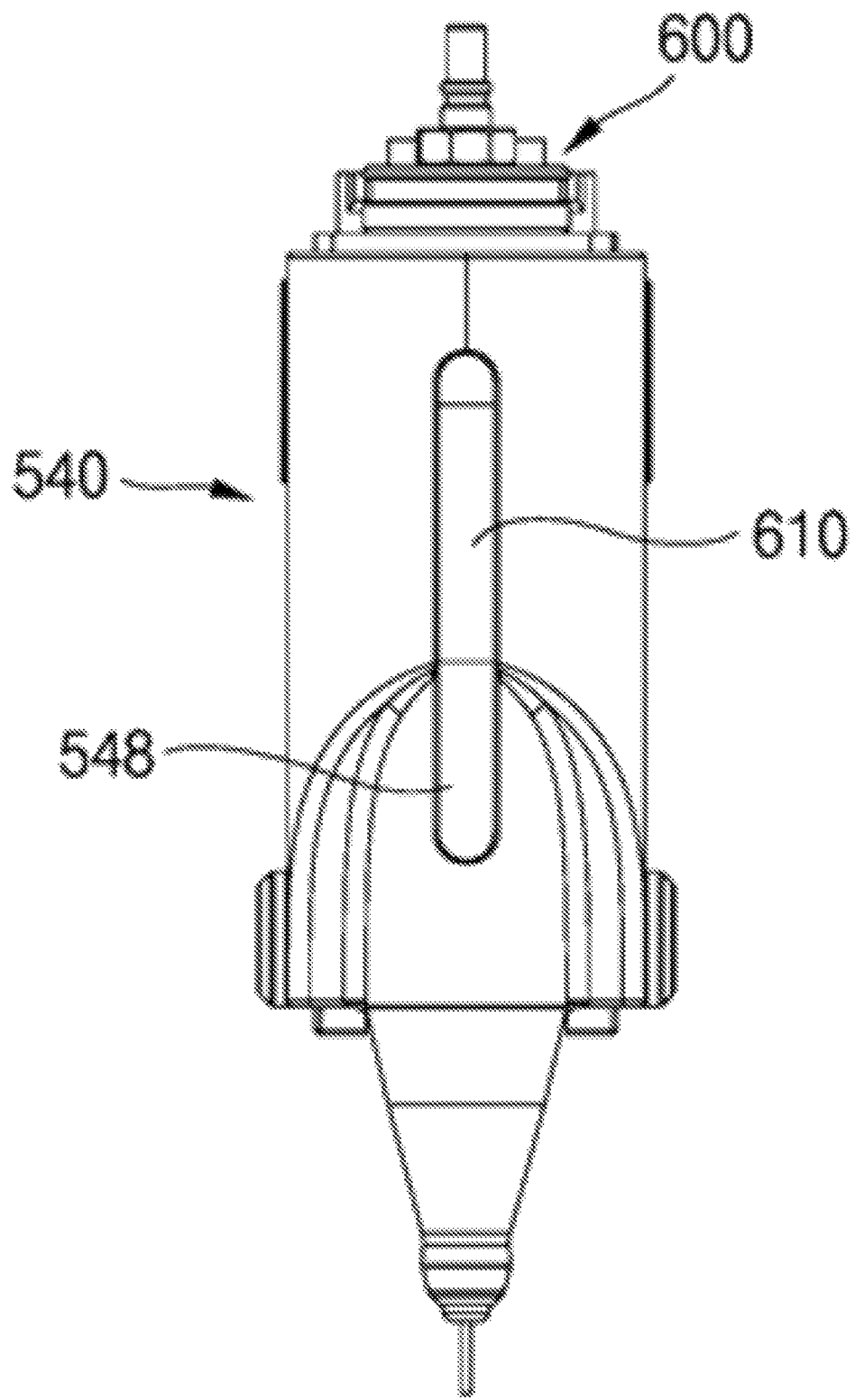

[Fig. 14]
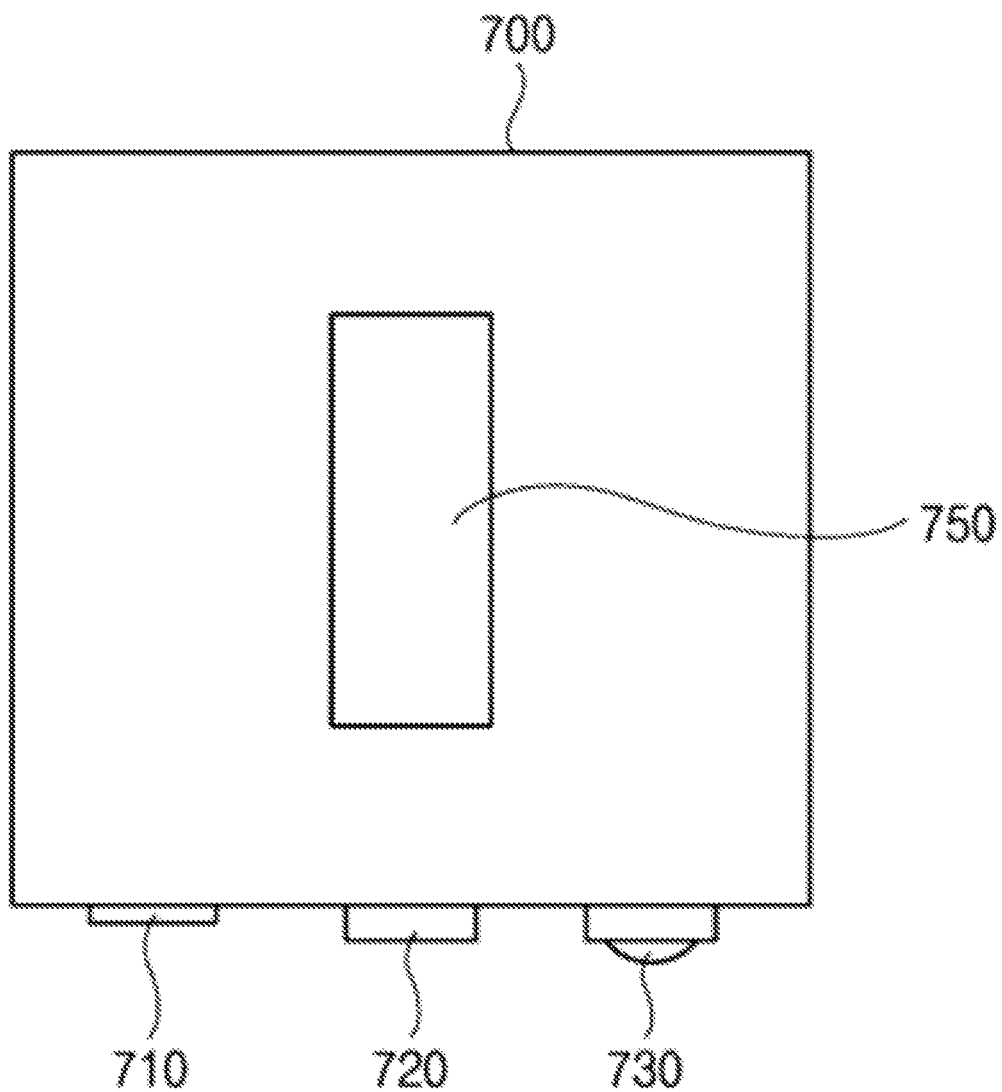

[Fig. 15]
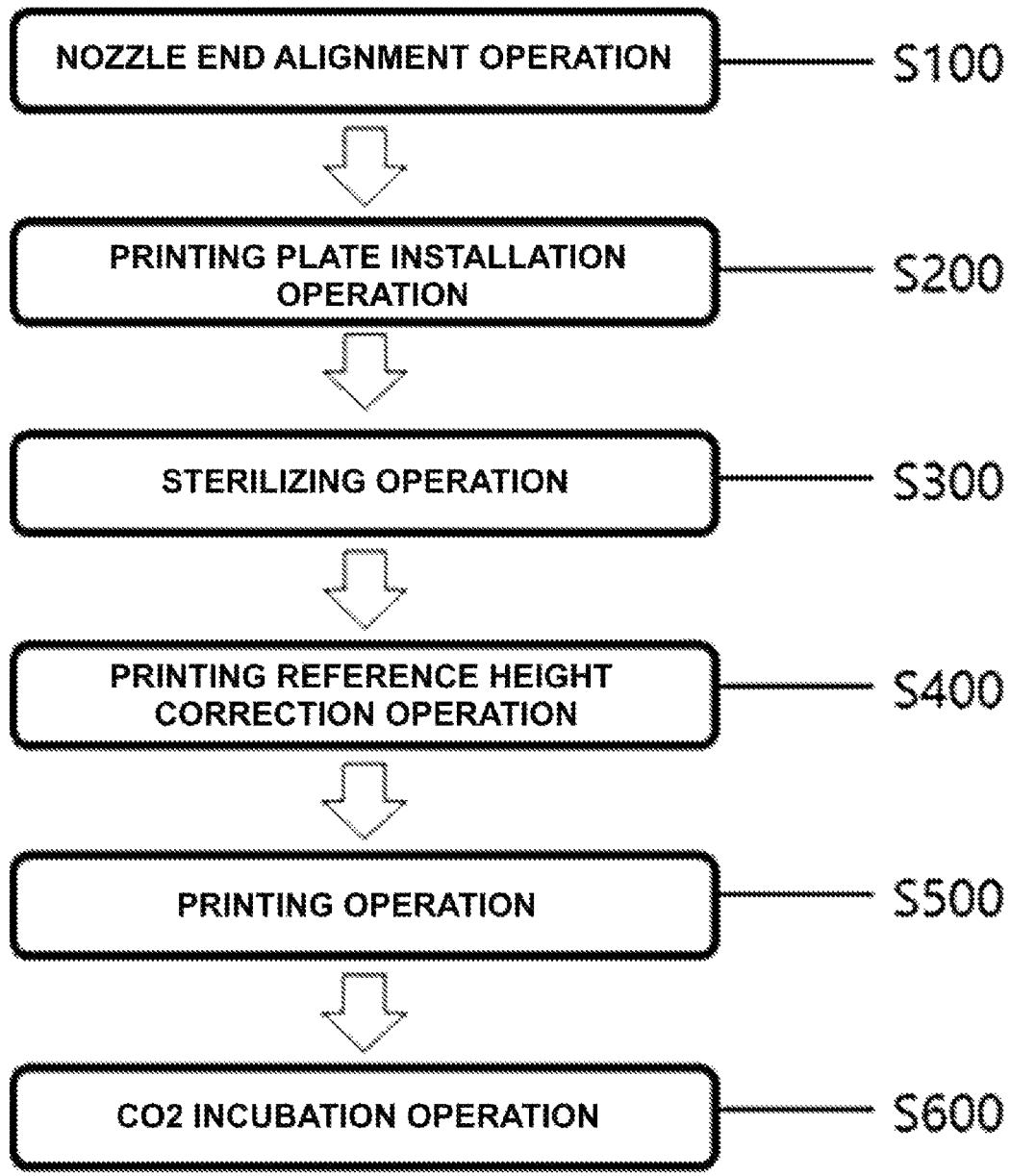

[Fig. 16]
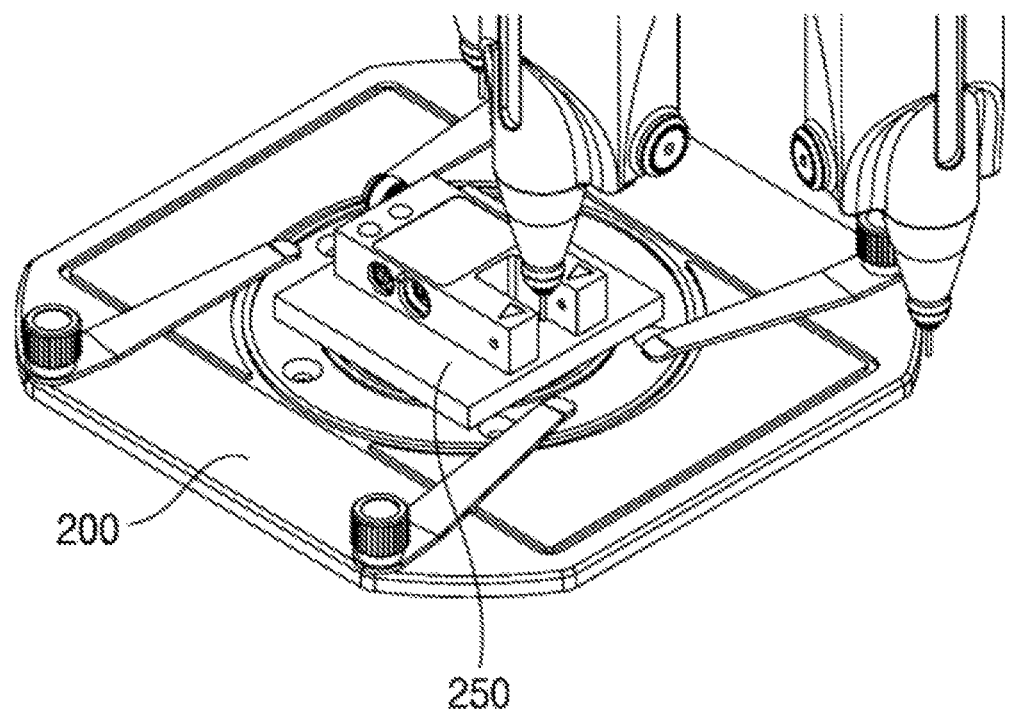

3D BIOPRINTER

BACKGROUND OF THE INVENTION

The present invention relates to a three-dimensional (3D) bioprinter, and more specifically, to a 3D bioprinter including a printing chamber capable of providing a sealed printing environment.

Recently, owing to the increased demand for research fields of tissue engineering and regenerative medicine and customized medical services, studies on three-dimensional (3D) printers using biomaterials are actively being conducted.

A known 3D printer includes a frame constituting an XYZ axes and a nozzle having a dispenser form for discharging a biomaterial. In such a conventional printer, the nozzle is filled with the biomaterial having viscosity, such as collagen or gelatin, in a fluid state. The conventional printer is used through a method in which the nozzle filled with the biomaterial in the fluid state is connected to a pneumatic system to push out and discharge the biomaterial.

However, in the case of such a discharge method, when a biomaterial is not in a fluid state, a nozzle should be heated at a high temperature to convert the state of the biomaterial to be a fluid state and discharge the biomaterial. Accordingly, since a process of heating and cooling the nozzle should be repeated in order to use both of a fluid-state biomaterial and a solid-state biomaterial, a problem may occur due to overload of the nozzle.

In order to solve such a problem, a 3D bioprinter including a first nozzle configured to output a solid-state material for forming a scaffold and other structures and a second nozzle configured to output a biomaterial (bio-ink) in a fluid state is disclosed in Korean Patent No. 10-1828345.

BRIEF SUMMARY OF THE INVENTION

The present invention is directed to providing a three-dimensional (3D) bioprinter including a print module capable of outputting a solid-state biomaterial and a fluid-state biomaterial and a printing chamber capable of providing a sealed printing environment.

The present invention is also directed to providing a 3D bioprinter including a printing chamber capable of providing a sealed printing environment to allow a living tissue to be printed in a sterile environment and CO2 incubation to be performed without moving the printed living tissue.

The present invention is also directed to providing a 3D bioprinter in which a plurality of syringes filled with fluid-state biomaterials are installed in a printing preparation operation, wherein each of the syringes is capable of outputting the biomaterials according to preset output conditions.

One aspect of the present invention provides a 3D bioprinter including a case, a printing chamber provided in the case, surrounded by wall surfaces so that an interior thereof is isolatable from the outside, and provided with a chamber door, a moving unit including a horizontal moving unit installed in a space under a bottom surface of the printing chamber and a vertical moving unit installed outside a side surface of the printing chamber, a bed supported by the horizontal moving unit to be disposed above a bottom surface opening and installed to be movable in X-axis and Y-axis directions, wherein the bottom surface opening is formed in the bottom surface of the printing chamber, a first bellows which covers a space between the bed and an inner circumferential surface of the bottom surface opening to isolate the interior of the printing chamber from the space under the bottom surface of the printing chamber and is deformed according to movement of the bed to allow the bed to be moved in the X-axis and Y-axis directions, a first print module provided in the printing chamber and installed to be vertically movable by the vertical moving unit in a Z-axis direction, a second print module provided at one side of the first print module in the printing chamber and installed to be vertically movable by the vertical moving unit in the Z-axis direction, and a controller configured to control operation of the moving unit, operation of the first print module, and operation of the second print module.

The 3D bioprinter may further include a hollow tube which extends through a side surface opening formed in the printing chamber, is supported by the vertical moving unit, and is installed to be movable in the Z-axis direction, and a second bellows which covers a space between an outer circumferential surface of the hollow tube and an inner circumferential surface of the side surface opening to isolate the interior of the printing chamber from an outside of the side surface of the printing chamber and is deformed according to movement of the hollow tube to allow the hollow tube to be moved in Z-axis direction, wherein the first print module may be connected to the hollow tube to be vertically moved with the hollow tube.

The 3D bioprinter may further include a blocking plate which closes an end portion of the hollow tube, wherein the first print module may be installed on the blocking plate to be replaceable, and a connector may be formed on the hollow tube or the blocking plate.

The 3D bioprinter may further include a temperature controller configured to adjust an internal temperature of the printing chamber, wherein the temperature controller may include a water jacket formed outside the wall surface of the printing chamber and configured to accommodate water and a heater configured to provide heat into the water jacket.

The 3D bioprinter may further include an air circulator configured to circulate air in the printing chamber, and a humidity controller configured to adjust an internal humidity of the printing chamber, wherein the air circulator may include an inlet through which air is introduced from the printing chamber, an air duct through which the air introduced through the inlet moves, an outlet formed as an opening provided in the side surface of the printing chamber, and a filter configured to filter the circulating air, and the humidity controller may include a tray configured to accommodate water to be provided to a side of the outlet.

The humidity controller may include a heating element disposed under the bottom surface of the printing chamber and configured to heat the water contained in the tray.

The air duct of the air circulator may extend through an interior of the water jacket.

A sterilization gas inlet and a sterilization gas outlet may be formed in the printing chamber, the printing chamber may be connected to a sterilization gas generator disposed outside the printing chamber through the sterilization gas inlet to allow sterilization in the printing chamber, and a sterilization gas may be exhausted through the sterilization gas outlet.

An incubation gas inlet and an incubation gas outlet may be formed in the printing chamber, and the printing chamber may be connected to a $CO_2$ tank through the incubation gas inlet so that an internal $CO_2$ concentration thereof may be controllable.

A center module, in which an ultrasonic level sensor configured to measure an actual height profile of a bottom surface of a printing plate installed on the bed is installed, may be provided between the first print module and the second print module.

A center module, in which a high definition camera configured to function as a microscope configured to observe a printout on a printing plate installed on the bed is installed, may be provided between the first print module and the second print module.

The second print module may include a syringe holder in which a syringe filled with a fluid-state biomaterial is installed, wherein the syringe holder may include a heating element and a cooling block configured to adjust a temperature of the syringe.

A reader configured to read information of a tag attached to the syringe installed in the syringe holder may be provided in the printing chamber, and the controller may be configured to control the temperature and an output of the syringe according to the information read by the reader.

The 3D bioprinter may further include a hollow cylindrical part fixed to an upper surface opening of the printing chamber and having open upper and lower ends, and a packing plate which is installed in the cylindrical part and divides the cylindrical part into an upper section and a lower section isolated from each other, wherein the second print module may be disposed under the packing plate.

The second print module may include a plurality of syringe holders disposed in a circumferential direction wherein syringes filled with fluid-state biomaterials are each installed in one of the plurality of syringe holders, and the 3D bioprinter may further include a rotary shaft of which one end is fixed to the packing plate and which extends upward, a rotary shaft support part which rotatably supports the rotary shaft, a support of which one end is fixed to the rotary shaft support part and the other end is fixed to the vertical moving unit to allow the rotary shaft to move vertically, and a rotary shaft driving motor configured to rotate the rotary shaft. The rotary shaft driving motor of the support may include an encoder motor, a potentiometer may be installed on the support, a pulley, which is positioned on an upper surface of the support, may be included in each of an end portion of the rotary shaft, an end portion of the potentiometer, and an end portion of the encoder motor, and timing belts may be installed between the pulley of the end portion of the rotary shaft and the pully of the end portion of the potentiometer and between the pully of the end portion of the potentiometer and the pully of the end portion of the encoder motor.

The 3D bioprinter may further include a syringe holder moving shaft of which a lower end is fixed to the syringe holder and which passes through the packing plate and extends upward, a fixed guide which is fixed to an upper surface of the packing plate and through which the syringe holder moving shaft passes, a moving guide fixed to an upper portion of the syringe holder moving shaft and configured to move the syringe holder moving shaft from a standby height to a printing start height, a spring configured to move the moving guide upward when an external force, by which the moving guide is moved downward, is not applied to the moving guide, a cam configured to rotate to push the moving guide of the syringe holder, which is moved to a printing position, downward to the printing start height, and a cam driving motor configured to drive the cam.

The 3D bioprinter may further include a magnet attached to the moving guide of each of the syringe holders, and a magnetoresistive (MR) sensor configured to detect the magnet attached to the moving guide of the syringe holder to detect whether the syringe holder rotates and moves to the printing position.

According to the present invention, since a living tissue can be printed without opening a printing chamber in a state in which the printing chamber is sealed, contamination which can occur during printing operations can be prevented. In addition, since an incubation operation can be performed in a non-stop manner after the living tissue is printed, there is an advantage in that cells can be grown immediately after the bioprinting.

Since a plurality of biomaterials can be output in the state in which the printing chamber is sealed when the living tissue is printed, various applications are possible and external contamination can be prevented.

There is an advantage in that sterilization can be performed and the living tissue can be printed in a state in which an interior of the printing chamber is isolated from the outside.

BRIEF DESCRIPTION OF THE DRAWINGS

FIG. 1 is a perspective view illustrating an exterior of a three-dimensional (3D) bioprinter according to an embodiment of the present invention.

FIG. 2 is a perspective view illustrating an exterior of a printing chamber provided in the 3D bioprinter according to the embodiment of the present invention.

FIG. 3 is a front view illustrating an interior of the printing chamber according to the embodiment of the present invention.

FIG. 4 is a longitudinal cross-sectional view illustrating the printing chamber according to the embodiment of the present invention in a state in which some components are removed.

FIG. 5 is a lateral cross-sectional view illustrating the printing chamber according to the embodiment of the present invention in a state in which some components are removed.

FIG. 6 is a cross-sectional view for describing an installation structure of a bed in the printing chamber according to the embodiment of the present invention.

FIG. 7 is a view illustrating a moving unit of the 3D bioprinter according to the embodiment of the present invention, wherein the moving unit is installed in a case.

FIG. 8 is a view for describing an installation structure of a second print module according to the embodiment of the present invention.

FIG. 9 is a view for describing an arrangement of a magnet and a magnetoresistive (MR) sensor for detecting a selected syringe holder, which moves to a printing position, in the second print module according to the embodiment of the present invention.

FIG. 10 is a view illustrating an arrangement of the syringe holder in the second print module according to the embodiment of the present invention.

FIG. 11 is a perspective view illustrating the syringe holder in an open state according to the embodiment of the present invention.

FIG. 12 is a cross-sectional view illustrating the syringe holder in a closed state according to the embodiment of the present invention.

FIG. 13 is a front view illustrating the syringe holder in the closed state according to the embodiment of the present invention.

FIG. 14 is a view for describing a center module according to the embodiment of the present invention.

FIG. 15 is a flowchart for describing a method of controlling the 3D bioprinter according to the embodiment of the present invention.

FIG. 16 is a view for describing a nozzle end alignment operation according to the embodiment of the present invention.

DETAILED DESCRIPTION OF THE INVENTION

Hereinafter, embodiments of the present invention will be described in detail with reference to the accompanying drawings. However, various embodiments of the present invention may be implemented in several different forms and are not limited to embodiments described herein. In addition, the accompanying drawings are only for the purpose of facilitating understanding of the embodiments disclosed herein, the technical spirit described in the specification is not limited to the accompanying drawings, and the present invention should be understood to cover all modifications, equivalents, and alternatives falling within the spirit and scope of the invention. In addition, parts irrelevant to descriptions are omitted in the drawings in order to clearly explain the present invention, sizes and shapes of components illustrated in the drawings are variously changed.

Suffixes such as "module" and "part" for elements used in the following description are given or mixed only in consideration of ease of specification descriptions and do not have their own meanings or roles. In addition, when it is determined that detailed descriptions of related well-known functions and configurations unnecessarily obscure the gist of the invention, the detailed descriptions will be omitted.

Throughout this specification, when a part is referred to as being "connected (coupled or fixed)" to another part, it includes "directly connected (coupled or fixed)" and "indirectly connected (coupled or fixed)" via an intervening part.

The terminology used herein to describe the embodiments of the present invention is not intended to limit the scope of the present invention. The articles "a," "an," and "the" are singular in that they have a single referent, however the use of the singular form in the present document does not preclude the presence of more than one referent unless the context clearly indicates otherwise. It should be further understood that the terms "comprise," "comprising," "include," and/or "including," when used herein, specify the presence of stated features, numbers, steps, operations, elements, and/or components, but do not preclude the presence or addition of one or more other features, numbers, steps, operations, elements, components, and/or groups thereof.

In addition, it will be understood that, although the terms "first," "second," and the like may be used herein to describe various elements, these elements should not be limited by these terms. These terms are only used for distinguishing one element from another. For example, a first element could be named a second element, and a second element could similarly be named a first element without departing from the scope of the present invention.

A three-dimensional (3D) bioprinter according to an embodiment of the present invention may include a case 10, a printing chamber 100, a bed 200, a moving unit 300, a first print module 400, a second print module 500, a center module 700, and a controller 900.

The controller 900 is for controlling the operation of the 3D bioprinter and includes an operation part, a memory, and wired and wireless interfaces for communicating with various sensors and peripheral devices. In FIG. 1, the controller 900 is illustrated to be disposed outside the case 10 but may be embedded in the case of the 3D bioprinter 1.

FIG. 1 is a perspective view illustrating an exterior of the 3D bioprinter according to the embodiment of the present invention.

As shown in FIG. 1, the case 10 includes an upper surface, a lower surface, and side surfaces so that an interior thereof is surrounded by the surfaces, and a case door 12 is installed in a front surface of the case 10. A transparent window 14 allowing the printing chamber 100 inside the case 10 to be observed from the outside is provided in the case door 12.

According to the embodiment of the present invention, since a double door type having the case door 12 and a chamber door 110 is used in the 3D bioprinter, the 3D bioprinter is advantageous for isolating an interior of the printing chamber 100 from the outside thereof.

FIG. 2 is a perspective view illustrating an exterior of the printing chamber provided in the 3D bioprinter according to the embodiment of the present invention, FIG. 3 is a front view illustrating the interior of the printing chamber according to the embodiment of the present invention, FIG. 4 is a longitudinal cross-sectional view illustrating the printing chamber according to the embodiment of the present invention in a state in which some components are removed, FIG. 5 is a lateral cross-sectional view illustrating the printing chamber according to the embodiment of the present invention in a state in which some components are removed, and FIG. 6 is a cross-sectional view for describing an installation structure of the bed in the printing chamber according to the embodiment of the present invention.

The printing chamber 100 is provided in the case 10. The printing chamber 100 is formed to be surrounded by wall surfaces, that is, a bottom surface 101, an upper surface 104, and side surfaces 106, so that an interior thereof is isolatable from the outside. The chamber door 110 including a transparent window 112 is installed in a front surface of the printing chamber 100.

According to the embodiment of the present invention, the printing chamber 100 includes a temperature controller 120, a humidity controller 130, and an air circulator 140 and is formed to allow air purification, temperature control, and humidity control to be performed in a state in which a printing space in the printing chamber 100 is sealed.

The temperature controller 120 includes a water jacket 122 formed outside a side surface 106 of the printing chamber 100 and a heater 124 installed on an outer wall of the water jacket 122.

The water jacket 122 is a chamber formed to surround an outer wall of the side surface 106 of at least one portion of the printing chamber 100 and accommodates water therein. The heater 124 is installed on the outer wall of the water jacket 122. The heater 124 heats the water in the water jacket 122 so that a temperature of the printing chamber 100 is adjustable. The controller 900 receives a sensing value from a temperature sensor (not shown) configured to detect an internal temperature of the printing chamber 100 to control the heater 124 to be turned on or off.

The humidity controller 130 provides moisture in the printing chamber 100 to adjust humidity therein. According to the embodiment of the present invention, the humidity controller 130 is provided on an air circulation passage generated by the air circulator 140. The air circulator 140 is for circulating, filtering, and purifying air in the printing chamber 100.

According to the embodiment of the present invention, the air circulator 140 includes an inlet 141, an air duct 142, an outlet 144, a filter 146 configured to filter and purify circulating air, and a blade (not shown) configured to generate an air circulation flow.

The inlet 141 is formed at one side of an upper surface 104 of the printing chamber 100. As the filter 146 such as a high-efficiency particulate air (HEPA) filter is installed in the inlet 141, the inlet 141 may remove contaminants contained in air to be introduced from the printing chamber 100.

The blade configured to generate the air circulation flow is installed in a blade installation part 148 in the air duct 142 formed adjacent to the inlet 141. The blade is rotated by a motor 149 disposed outside the air duct 142. Contaminants such as particles generated when the motor 149 is driven may be blocked.

According to the embodiment of the present invention, the humidity controller 130 is formed to use air circulation generated by the air circulator 140.

According to the embodiment of the present invention, the humidity controller 130 includes a tray 132 which accommodates water therein, and the tray 132 is provided at a side of the outlet 144.

The tray 132 is installed at the outlet 144 having an opening form. Since the tray 132 which accommodates water is provided at the side of the outlet 144, the water accommodated in the tray 132 is induced to be vaporized and diffused by circulation air introduced into the printing chamber 100 through the outlet 144. In addition, the humidity controller 130 may include a heating element 134 installed under the tray 132 and heat water stored in the tray 132 with a small amount of heat to quickly adjust humidity.

The heating element 134 is disposed under a bottom surface of the printing chamber 100 to correspond to a bottom surface of the tray 132. Accordingly, cables such as power lines and control lines may be connected to the heating element 134 from the outside of the printing chamber 100. The heating element 134 is controlled by the controller 900 configured to receive a sensing signal of a sensor (not shown) configured to detect an internal humidity of the printing chamber 100.

According to the embodiment of the present invention, the air duct 142 extends into the water jacket 122. Referring to the drawings, the air duct 142 is formed along a passage extending from the upper surface toward a lower portion of the side surface of the printing chamber 100 and passes through an interior of the water jacket 122 to extend downward. Such an arrangement of the air duct 142 is more advantageous for adjusting a temperature of the printing chamber 100.

A light-emitting diode (LED) light (not shown) and an ultraviolet (UV) lamp (not shown) may be installed in the printing chamber 100. The UV lamp may be used to sterilize harmful microorganisms in the printing chamber 100.

According to the embodiment of the present invention, the printing chamber 100 is formed to be capable of printing in the printing chamber in a state in which the interior of the printing chamber is sterilized. To this end, the printing chamber 100 is formed to be connected to a sterilization gas generator to perform a sterilizing operation therein. The sterilization gas generator includes a $H_2O_2$ plasma sterilizer 165 and is provided outside the printing chamber 100.

A sterilization gas inlet 162 and a sterilization gas outlet 164 are formed in the printing chamber 100. The sterilization gas inlet 162 is a passage through which a $H_2O_2$ sterilization gas is introduced from the $H_2O_2$ plasma sterilizer 165, and the sterilization gas outlet 164 is used to exhaust the internal $H_2O_2$ sterilization gas after the sterilizing operation.

The sterilization may be performed before printing is performed in a state in which a printing plate 201 for supporting a printout is installed on the bed 200 of the printing chamber 100. When a sterilization command is input, the $H_2O_2$ sterilization gas generated by the $H_2O_2$ plasma sterilizer 165 is introduced into the printing chamber 100 through the sterilization gas inlet 162, and the sterilizing operation proceeds for a predetermined time. Next, a ventilating operation through which the $H_2O_2$ sterilization gas is exhausted through the sterilization gas outlet 164 is performed.

According to the embodiment of the present invention, the printing chamber 100 is formed so that the printout is printed, and $CO_2$ incubation is allowed in a non-stop manner. To this end, an incubation gas inlet 172 and an incubation gas outlet 174 for forming the interior of the printing chamber 100 with a $CO_2$ incubation atmosphere are formed in the printing chamber 100. The incubation gas inlet 172 is connected to a regulator (not shown) and a $CO_2$ tank 175 to allow $CO_2$ gas to be introduced into the printing chamber 100 so as to adjust an internal concentration of carbon dioxide in the printing chamber 100. The incubation gas outlet 174 is a passage through which internal air is exhausted to adjust the internal $CO_2$ concentration in the printing chamber 100.

In order to perform the incubation after a living tissue is printed, an environment in which a carbon dioxide concentration ranges from 3 to 5%, a temperature is about 37° C., and a humidity is about 80% is required. The $CO_2$ incubation denotes incubation performed while a concentration of carbon dioxide is adjusted.

According to the present invention, since the printing chamber 100 is formed to have a structure which may be sealed from the outside and allows the carbon dioxide concentration to be adjustable for the $CO_2$ incubation, the $CO_2$ incubation may be performed without changing a place after the living tissue is printed.

The bed 200 installed to be movable in an X-axis direction and a Y-axis direction is provided at the bottom surface of the printing chamber 100 according to the embodiment of the present invention.

According to the embodiment of the present invention, a bottom surface opening 102 is formed in a bottom surface 101 of the printing chamber 100, and the bed 200 is disposed above the bottom surface opening 102. The bed 200 moves within a moving region allowed by the bottom surface opening 102. An upper surface of the bed 200 is formed to allow the printing plate 201 on which the printout is printed to be fixed at a predetermined position.

The bed 200 is connected to a horizontal moving unit 310 installed in a lower portion of the printing chamber 100. The horizontal moving unit 310 is connected to the bed 200 to move the bed 200 in the X-axis direction and the Y-axis direction. A lower part of the bed 200 is fixed to the horizontal moving unit 310. In the present specification, the bed 200 includes both of a part disposed in the printing chamber and coupled to the printing plate 201 and the lower part connected to the horizontal moving unit 310.

According to the embodiment of the present invention, a first bellows 210 is installed between the lower part of the bed 200 and an inner circumferential surface of the bottom surface opening 102. The bed 200 is disposed above a central hole 211 of the first bellows 210, and the lower part thereof extends downward from the first bellows 210 through the central hole 211 and is connected to the horizontal moving unit 310. A circumferential surface of the central hole 211 is fixed to the lower part of the bed 200 to be sealed. Accordingly, the first bellows 210 covers a space between the bed 200 and the inner circumferential surface of the bottom surface opening 102 and isolates the interior of the printing chamber from a space under the bottom surface of the printing chamber. Accordingly, particles generated when the horizontal moving unit 310 moves or external contaminants may be prevented from being introduced through the bottom surface opening 102. That is, movement of foreign materials between upper and lower portions of the first bellows 210 is prevented. In addition, since the first bellows 210 is deformed due to flexibility thereof, the bed 200 is allowed to move in the X-axis direction and the Y-axis direction.

FIG. 7 is a view illustrating the moving unit of the 3D bioprinter according to the embodiment of the present invention, wherein the moving unit is installed in the case.

As shown in FIG. 7, the moving unit 300 according to the embodiment of the present invention includes the horizontal moving unit 310 horizontally disposed to move in the X-axis direction and the Y-axis direction and vertical moving units 350 and 360 which move in a Z-axis direction.

The horizontal moving unit 310 is disposed in the space under the bottom surface of the printing chamber 100 in the case 10.

The horizontal moving unit 310 includes a first horizontal moving unit 320 which moves in the X-axis direction and a second horizontal moving unit 330 which is disposed on an upper portion of the first moving unit and moves in the Y-axis direction. In a case in which the first horizontal moving unit 320 performs driving in the Y-axis direction, the second horizontal moving unit 330 is installed to move in the X-axis direction.

Each of the first horizontal moving unit 320 and the second horizontal moving unit 330 includes a guide rail and a step motor. When the step motor of the first horizontal moving unit 320 is controlled to be driven by the controller 900, the second horizontal moving unit 330 supported by an upper portion of the guide rail moves in the X-axis direction. The second horizontal moving unit 330 is disposed above the first horizontal moving unit 320 and moves in the Y-axis direction.

The bed 200 is fixed to a moving plate supported by the guide rail of the second horizontal moving unit 330. Movement of the bed 200 in the X-axis and the Y-axis directions is controlled by movement of the first horizontal moving unit 320 and movement of the second horizontal moving unit 330.

According to the embodiment of the present invention, the vertical moving units 350 and 360 include a first vertical moving unit 350 and a second vertical moving unit 360 and are installed outside the side surface of the printing chamber.

The first vertical moving unit 350 controls the first print module 400 to move in the Z-axis direction, that is, vertical movement thereof, and the second vertical moving unit 360 controls the second print module 500 to move in the Z-axis direction, that is, vertical movement thereof. Each of the first and second vertical moving units 350 and 360 includes a guide rail and a step motor. The first print module 400 and the second print module 500 are connected to moving plates supported by the guide rails.

A hollow tube 410 is fixed to the moving plate of the first vertical moving unit 350, and the hollow tube 410 is connected to the first print module 400 so that vertical movement of the first print module 400 is controlled.

A support 480 supporting the second print module 500 is fixed to a moving plate 362 of the second vertical moving unit 360 so that vertical movement of the second print module 500 is controlled.

The first print module 400 and the second print module 500 are provided in the printing chamber 100 according to the embodiment of the present invention.

A fixing structure of the first print module 400 will be described with reference to FIGS. 2 to 7.

The first print module 400 may be provided to output a solid-state biomaterial for printing a structure such as a scaffold, a pharmaceutical structure, and a frame structure. For example, an extruder module which outputs a filament, a hot melting module which is a high pressure melting injector which is filled with a medicine or granular polymer material, melts the medicine or granular polymer material with high heat, and pneumatically outputs the medicine or granular polymer material may be used as the first print module 400. However, the first print module is not limited to outputting a first solid-state biomaterial. Meanwhile, the solid-state biomaterial denotes a material which maintains a solid-state when cured, and the biomaterial includes various materials usable for bio-related printouts but is not limited to specific materials.

In the fixing structure of the first print module 400, a side surface opening 107 is formed in the side surface 106, which faces the door 110, of the printing chamber 100. The hollow tube 410 extends into the printing chamber 100 through the side surface opening 107. The hollow tube 410 is supported by the moving plate of the first vertical moving unit 350 to move in the Z direction, that is, a vertical direction.

A second bellows 420 which divides an inner portion from an outer portion of the side surface opening 107 is installed between an outer circumferential surface of the hollow tube 410 and an inner circumferential surface of the side surface opening 107. The hollow tube 410 extends into the printing chamber 100 in a state in which the outer circumferential surface of the hollow tube 410 is surrounded by an inner circumferential surface of the second bellows 420. Accordingly, the second bellows 420 covers a space between the outer circumferential surface of the hollow tube 410 and the inner circumferential surface of the side surface opening 107 to isolate the interior of the printing chamber from the outside of the printing chamber.

The second bellows 420 allows the hollow tube 410 to vertically move in the Z-axis direction due to flexibility thereof and also prevents external contaminants such as particles from being introduced through the side surface opening 107.

A blocking plate 415 is provided on a front surface of the hollow tube 410. The first print module 400 is installed on the blocking plate 415 to be replaceable. The blocking plate 415 blocks external contaminants from being introduced through an interior of the hollow tube 410 and allows the first print module 400 to be easily replaced.

Cables such as power lines and control lines required to drive the first print module 400, air tubes for applying pneumatic pressure, hose tubes such as cooling water tubes, and the like are introduced into the printing chamber 100 through the interior of the hollow tube 410, and a connector 417 is connected to the blocking plate 415 and/or a circumferential surface of the hollow tube 410. The connector 417 prevents foreign materials from being introduced and is a passage through which the cables, hose tubes, and the like are connected to the interior. The first print module 400 may receive power, control signals, air, coolants from external devices through the connector 417.

Since the extruder module, the hot melting module, or the like used as the first print module 400 is installed on the blocking plate 415, movement of the extruder module, the hot melting module, or the like is controlled by movement of the hollow tube 410.

As shown in FIG. 3, the second print module 500 is disposed at one side of the first print module 400.

According to the embodiment of the present invention, the second print module 500 includes syringe holders 540 in which syringes 600 filled with fluid-state biomaterials are installed.

According to the embodiment of the present invention, the second print module may include one syringe holder. In this case, the second print module may also have a vertical movement structure which is the same as or similar to that of the first print module.

The second print module according to the embodiment of the present invention will be described with reference to FIGS. 3, 4, and 7 to 13.

According to the embodiment of the present invention, the second print module 500 may include the plurality of syringe holders 540, the plurality of syringes 600 filled with different biomaterials may be each installed in one of the syringe holders 540, and the different biomaterials may be selectively output in preset order by the controller 900.

FIG. 8 is a view for describing an installation structure of the second print module according to the embodiment of the present invention.

According to the embodiment of the present invention, the second print module 500 includes five syringe holders 540 and is installed to be rotatable and vertically movable by a second print module support part.

The syringe holders 540 forming the second print module are disposed in a circumferential direction about a central line extending along a center of a rotary shaft 530 and are installed to be rotatable by the rotary shaft 530. In addition, the second print module 500 is installed to be connected to the second vertical moving unit 360 so that vertical movement of the entirety thereof is adjusted in the Z-axis direction and vertical movement of the syringe holder 540 positioned at a printing position is adjustable between a standby height and a printing start height.

In the present specification, when the second print module is described, the term "printing position" denotes a position on an XY coordinate system on which printing is performed by the syringe. The printing position is specified with specific coordinates. The syringe holders are controlled to rotate about the rotary shaft to move to the printing position, and the syringe is controlled to perform printing at the printing position.

At the printing position, vertical movement of the syringe holder may be controlled in the Z-axis direction. The syringe holder may have the standby height and the printing start height at the printing position. In a case in which printing is performed by the syringe installed in the syringe holder positioned at the printing position, first, the syringe holder moves downward to the printing start height from the standby height, and printing is performed by the syringe. The standby height of the selected syringe holder may be the same as a height of the nearby syringe holder. The printing start height denotes a height which is lower than the standby height, is positioned lower than the height of the nearby syringe holder which is not selected, and is not interfered with by the nearby syringe holder and the nearby syringe when the printing is performed.

According to the embodiment of the present invention, the second print module support part includes a hollow cylindrical part 510 (see FIG. 3), a packing plate 520, the rotary shaft 530, syringe holder support parts 550, and a syringe holder vertical movement driver 560.

The hollow cylindrical part 510 is formed to have open upper and lower ends and is fixed to an upper surface opening 105 of the printing chamber 100. An inner circumferential surface of the upper surface opening 105 is blocked from an outer circumferential surface of the hollow cylindrical part 510 so that contaminants are prevented from being introduced therebetween.

The packing plate 520 is installed in the hollow cylindrical part 510. The packing plate 520 divides an interior of the cylindrical part 510 into an upper section and a lower section isolated from each other. The packing plate 520 isolates the lower section, that is, a section positioned in the printing chamber, from the upper section connected to the outside to prevent contaminants from being introduced into the lower section from the upper section. The packing plate 520 is installed to be vertically movable and rotatable inside the cylindrical part 510. One end of the rotary shaft 530 is fixed to the packing plate 520, and the rotary shaft 530 extends upward. The packing plate 520 is rotated according to rotation of the rotary shaft 530, and the packing plate 520 is vertically moved according to vertical movement of the rotary shaft 530.

The rotary shaft 530 is rotatably supported by a rotary shaft support part 532 which rotatably surrounds the rotary shaft 530. Vertical movement of the rotary shaft 530 and vertical movement of the rotary shaft support part 532 are controlled at the same time.

Rotation of the rotary shaft 530 is controlled by a rotary shaft driver 590. According to the embodiment of the present invention, the rotary shaft driver 590 includes a support 591, a rotary shaft driving motor 592, and a potentiometer 593.

One side of the support 591 is fixed to the rotary shaft support part 532, and the support 591 extends therefrom. The support 591 is fixed to a moving plate of a second vertical moving unit 360. Accordingly, vertical movement of the second print module 500 may be controlled in the Z-axis direction.

The potentiometer 593 and the rotary shaft driving motor 592 are coupled to the support 591, and an end portion of the rotary shaft 530, an end portion of the potentiometer 593, and an end portion of the rotary shaft driving motor 592 protrude from an upper surface of the support 591.

Pulleys 595, 596, and 597 for timing belts are formed on the end portion of the rotary shaft 530, the end portion of the potentiometer 593, and the end portion of the rotary shaft driving motor 592. In addition, a timing belt is installed between the pulley 595 of the end portion of rotary shaft 530 and the pulley 596 of the end portion of the potentiometer 593, and a timing belt is installed between the pulley 596 of the end portion of the potentiometer 593 and the pulley 597 of the end portion of the rotary shaft driving motor 592. That is, two timing belts are installed on the pulley 596 of the end portion of the potentiometer 593.

An encoder motor is used as the rotary shaft driving motor 592. According to the embodiment of the present invention, when the encoder motor is used as the rotary shaft driving motor, and the potentiometer 593 is provided on a passage through which a rotating force of the encoder motor is transferred to the rotary shaft, rotation of the encoder motor is accurately detected by the potentiometer, and thus a rotation angle of the rotary shaft is more precisely controllable.

The plurality of syringe holders 540 are disposed under the packing plate 520 to be spaced apart from each other along the circumference about the central line of the rotary shaft 530.

The syringe holders 540 are supported by the syringe holder support parts 550. According to the embodiment of the present invention, the syringe holder support part is provided to control the syringe holder 540 to vertically move between the standby height and the printing start height.

According to the embodiment of the present invention, the syringe holder support part 550 includes a syringe holder moving shaft 552, a fixed guide 551, a guide shaft 554, a moving guide 556, and a spring 558.

The syringe holder moving shaft 552 passes through the packing plate 520, extends from the upper section to the lower section, and is installed to be vertically movable in the Z-axis direction. The syringe holder 540 is supported by a lower end of the syringe holder moving shaft 552.

The fixed guide 551 is fixed to an upper surface of the packing plate 520, and the syringe holder moving shaft 552 passes through and is guided by the fixed guide 551.

The moving guide 556 is fixed to an upper portion of the syringe holder moving shaft 552. The syringe holder moving shaft 552 is vertically moved by vertical movement of the moving guide 556, and the syringe holder 540 is controlled to be vertically moved between the standby height and the printing start height.

Movement of the moving guide 556 is guided by the guide shaft 554. A lower end of the guide shaft 554 is fixed to the fixed guide 551, and the guide shaft 554 extends upward therefrom. An upper portion of the guide shaft 554 is inserted into a through hole formed in the moving guide 556 to be vertically movable. Since the guide shaft 554 is installed to pass through the moving guide 556, vertical movement is performed at an aligned position by the guide shaft 554.

The spring 558 is installed on the guide shaft 554 or the syringe holder moving shaft 552. The spring 558 provides an elastic force so that the moving guide 556 is moved upward when an external force is not applied to move the moving guide 556 downward. That is, when the external force is not applied thereto, the syringe holder 540 is moved upward to the standby height by the spring 558 and remains at the standby height.

The syringe holder vertical movement driver 560 includes a cam 562 and a cam driving motor 564.

The cam 562 is installed to push the moving guide 566 downward at the printing position. The cam driving motor 564 is controlled by the controller 900 to rotate the cam 562 so as to push the moving guide 566 downward. When the cam 562 is rotated, and the moving guide 566 is pushed downward, the syringe holder 540 positioned at the printing position is moved downward from the standby height to the printing start height. The entirety of the second print module 500 is controlled to be vertically moved in the Z-axis direction, a Z coordinate of the printing start height may be changed. However, a distance between the standby height and the printing start height from the packing plate 520 is constant.

The cam 562 and the cam driving motor 564 are supported by the rotary shaft support part 532 through a bracket and the like and vertically moved with the rotary shaft support part 532.

According to the embodiment of the present invention, a detector configured to detect whether the selected syringe holder 540 moves to the printing position is provided. The detector includes a magnet 571 attached to each of the moving guides 566 and a magnetoresistive (MR) sensor 572 installed on a bracket connected to the rotary shaft support part 532.

FIG. 9 is a view for describing an arrangement of the magnet and the MR sensor for detecting the selected syringe holder, which moves to the printing position, in the second print module according to the embodiment of the present invention.

When the rotary shaft 530 rotates and the selected syringe holder 540 moves to the printing position, the MR sensor 572 detects the magnet attached to the moving guide 566 to output a detection signal, and the controller 900 stops rotation of the rotary shaft 530 so that the selected syringe holder 540 remains at the printing position.

According to the embodiment of the present invention, the controller 900 designates the syringe holder, which is positioned at an initial origin, that is, a printing position before a printing operation is started by a print button being pushed, among the plurality of syringe holders, as a first syringe holder. Forward rotation and reverse rotation of the rotary shaft is controlled based on the first syringe holder.

According to the embodiment of the present invention, air tubes (not shown) pass through the packing plate 520 and extend to be connected to the syringes 600 installed in the syringe holders 540. In addition, cables, such as power lines and control lines, cooling water tubes, and like, for the syringe holders pass through the packing plate 520 and extend downward.

The syringe holder 540 moved to the printing position is moved downward from the standby height to the printing start height by the cam 562, and a biomaterial is output through an air dispensing process.

FIG. 10 is a view illustrating an arrangement of the syringe holder in the second print module according to the embodiment of the present invention.

In the present specification, a number for the syringe installed in the syringe holder is designated to be the same as a number for the syringe holder in which the syringe is installed. For example, the syringe installed in the first syringe holder is referred to as a first syringe, and the syringe installed in a second syringe holder is referred to as a second syringe.

When the second print module is positioned at an initial origin, that is, a home position, set in the encoder motor, the syringe holder, which is positioned at a printing position, of the second print module is defined as a first syringe holder 540-1.

According to the present invention, when an angle, at which the first syringe holder is positioned, of the rotary shaft is defined as 0°, a rotation angle of the rotary shaft is controlled to be 180° (degrees) or less in clockwise and counterclockwise directions. That is, forward rotation and reverse rotation are controlled on the basis of the first syringe holder 540-1, and the rotation angle is controlled to be 180° or less.

The next numbers are alternately designated to the syringe holders facing each other with respect to a reference line connecting the central line of the rotary shaft and a center of the first syringe holder. That is, when a rotational position of the first syringe holder 540-1 is defined as 0°, the second syringe holder 540-2 is positioned at a rotational position of $\alpha°$ with respect to the first syringe holder 540-1 in the clockwise direction, and a third syringe holder 540-3 is positioned at a rotational position of $\alpha°$ with respect to the first syringe holder 540-1 in the counterclockwise direction. In addition, a fourth syringe holder 540-4 is positioned at a rotational position of $(\alpha+\beta)°$ with respect to the first syringe holder 540-1 in the clockwise direction, and a fifth syringe holder 540-5 is positioned at a rotational position of $(\alpha+\beta)°$ with respect to the first syringe holder 540-1 in the counterclockwise direction.

Accordingly, for example, when it is assumed that biomaterials are sequentially output from the first syringe to the fifth syringe, after the biomaterial is output by the first syringe, the another syringes output bio-inks while the rotary shaft alternately rotates in the clockwise direction and the counterclockwise direction. Due to such an arrangement of the syringe holders 540, when the second print module is driven, twisting of wires, control lines, air tubes, and cooling water tubes connected to the second print module may be prevented.

FIGS. 10 and 11 are views for describing the syringe holder in the second print module according to the present invention, wherein FIG. 11 is a perspective view illustrating the syringe holder in an open state, and FIG. 12 is a cross-sectional view illustrating the syringe holder in a closed state. FIG. 13 is a front view illustrating the syringe holder in the closed state.

As shown in FIGS. 11 and 12, the syringe holder 540 according to the embodiment of the present invention includes a syringe holder body 541 and a syringe holder cover 547.

In the syringe holder body 541, a seating groove having a semicircular shape corresponding to a shape of the syringe 600 is formed at one side thereof. A heating element 543 is disposed in the seating groove 542 of the syringe holder. A Peltier element as a cooling element 544 corresponding to the heating element 543 is installed on an outer side surface of the syringe holder body 541, and a cooling block 545 for heat dissipating is attached to the Peltier element. Cooling fins are formed on the cooling block 545, and through holes 546 through which the cooling water tubes pass are formed in the cooling block 545 so that the cooling block 545 is cooled by the cooling water tube.

The syringe holder cover 547 is installed on the syringe holder body 541 to be openable and closable in a hinge manner. The syringe holder cover 547 is coupled to the syringe holder body 541 by a hinge shaft 549 provided at a lower side of the syringe holder cover 547. A syringe 600 is accommodated in the syringe holder cover 547 in an open state in which the syringe holder cover 547 is spaced apart from the syringe holder body 541 and rotated about a hinge to be closed.

A reading window 548 having a hole or transparent window form allowing a near field communication (NFC) tag 610 attached to the syringe installed therein to be observed from the outside is formed in the syringe holder cover 547.

In the syringe holder 540, a temperature of the syringe is controllable by the heating element 543, the cooling element 544, and the cooling block 545 according to the output conditions of the syringe accommodated in the syringe holder. The cooling element and/or the cooling block 545 forms a cooling part.

Referring to FIG. 13, according to the embodiment of the present invention, the NFC tag 610 on which an output condition of the biomaterial filling the syringe is described is attached to each of the syringes 600, and an NFC reader 750 which reads the NFC tag 610 of the syringe positioned at a printing position is provided in the printing chamber. In the printing chamber 100, the NFC reader 750 is provided on a side surface of the center module 700 disposed between the first print module 400 and the second print module 500.

When the syringe 600, which is selected to perform printing, in the second print module 500 moves to a printing position, the NFC reader 750 reads the NFC tag 610 attached to the syringe 600, and the heating element 543 and the cooling part provided in the syringe holder 540 are controlled to control a syringe temperature matching the read output conditions. Next, air is supplied to the syringe 600 to output the biomaterial according to the controlled output conditions.

According to the embodiment of the present invention, in the printing chamber 100, the center module 700 is provided between the first print module 400 and the second print module 500.

FIG. 14 is a view for describing the center module according to the embodiment of the present invention. The center module includes an ultrasonic level sensor 710, an UV curing device 720, and a high magnification camera module 730.

The ultrasonic level sensor 710 is used for measuring a leveling offset value of the printing plate 201 provided on the bed 200. The ultrasonic level sensor 710 is set based on an origin position of the bed 200.

A printing reference height is set in the controller 900 in consideration of a thickness, that is, a height, of the printing plate. The printing reference height is a height of a bottom surface on which a printout is printed, and a nozzle of the print module is controlled to move in the Z direction on the basis of the bottom surface.

However, in a case in which a height of the bottom surface of the printing plate 201 installed on the bed 200 is different from the preset printing reference height, or the bottom surface of the printing plate is not flat, is curved, or is not horizontal, print quality may be degraded.

The ultrasonic level sensor 710 scans the bottom surface of the printing plate to measure an actual height of the bottom surface of the printing plate. The actual height of the bottom surface is mapped by the ultrasonic level sensor 710. The controller 900 compares a profile of the actual height of the bottom surface of the printing plate and the preset printing reference height to calculate a leveling offset value and corrects the preset printing reference height using the calculated offset value. Printing may be performed on the basis of the corrected printing reference height.

The ultrasonic level sensor 710 is set on the basis of the origin position of the bed 200.

The UV curing device 720 may perform an UV curing operation on a corresponding layer which needs the UV curing operation when the biomaterials and other photocurable materials are output. The UV curing operation may be performed on each layer by the curing device.

The high magnification camera module 730 serves as a microscope allowing a printout such as a living tissue printed on the printing plate 201 and growth thereof to be monitored from the outside in a state in which the printing chamber 100 is not opened. The high magnification camera module 730 is connected to a monitoring system installed outside the printing chamber 100 and allows microscopic observation to be performed from the outside and a remote place through a monitor, an application, or the like.

Hereinafter, a method of controlling the 3D bioprinter will be described according to the embodiment of the present invention.

FIG. 15 is a flowchart for describing a method of controlling the 3D bioprinter according to the embodiment of the present invention.

As shown in FIG. 15, the method of controlling the 3D bioprinter according to the embodiment of the present invention includes a nozzle end alignment operation (S100), a printing plate installation operation (S200), a sterilizing operation (S300), a printing reference height correction operation (S400), a printing operation (S500), and a $CO_2$ incubation operation (S600).

The nozzle end alignment operation is performed after a printing preparation operation is performed.

The printing preparation operation includes a preparation operation performed for a general 3D bioprinter. In order for the 3D printer to perform printing, a printout should be modeled to prepare a 3D modeling file, the 3D modeling file should be converted to a G-code file thereof, and the G-code file should be input to the controller of the 3D printer. In addition, use materials and the method of printing the printout are determined, a determined moving passage of the nozzle is described in a G-code file thereof, and the G-code file is input to the 3D printer.

Next, the case door and the door are opened, the first print module and the syringes matching with the printout to be printed are installed. An extruder module or hot melting module may be installed as the first print module. In addition, the syringe holder covers of the syringe holders are opened and the syringes filled with selected bio-inks (fluid-state biomaterials) are installed. The NFC tag on which output conditions are recorded is attached to each of the syringes.

According to the embodiment of the present invention, after the printing preparation operation is performed, the nozzle end alignment operation (S100) is performed.

FIG. 16 is a view for describing the nozzle end alignment operation according to the embodiment of the present invention and shows a fork sensor installed on the bed 200. According to the present invention, the fork sensor is used as a nozzle end alignment sensor 250.

The nozzle end alignment operation (S100) includes an operation (a) in which the nozzle end alignment sensor is installed at a predetermined position on the bed in the printing chamber and a sensing point of the nozzle end alignment sensor is positioned at an origin position of the bed, an operation (b) in which the bed is moved toward one side in the X-axis direction and the sensing point of the nozzle end alignment sensor is positioned under the nozzle of the first print module, an operation (c) in which the first print module is moved downward and a Z value of the nozzle end of the first print module is measured, an operation (d) in which the first print module is positioned at an original position and the bed is moved toward the other side in the X-axis direction to position the sensing point of the nozzle end alignment sensor under the syringe, which is disposed at a printing position, of the second print module, an operation (e) in which the second print module is moved downward and a Z value of the nozzle end of the syringe, which is disposed at a printing position, of the second print module is measured, and an operation (f) in which the second print module is positioned at an original position and the bed is positioned at an original position.

In the nozzle end alignment operation (S100), the nozzle ends of the print modules are measured using the nozzle end alignment sensor 250 installed at the predetermined position of the bed 200 in the printing chamber 100. This operation is for measuring the nozzle ends of the extruder module or hot melting module selected as the first print module and the nozzle ends of all of the nozzles of the syringes installed in the second print module to align the nozzle ends.

When the first print module 400 and the second print module 500 are set, the nozzles of the print modules are set to be positioned at a predetermined position (X, Y). When the origin position of the bed is set to a position (0, 0), a position of the nozzle of the first print module 400 is set to a position ($X_1$, 0), and a position of the syringe nozzle, which is positioned at the printing position, of the second print module is set to a position ($X_2$, 0).

The nozzle end alignment operation (S100) is performed for measuring the nozzle ends in a state in which the first print module 400 and the second print module are set as described above.

The sensing point of the nozzle end alignment sensor 250 is positioned at the predetermined initial origin position of the bed 200, that is, a position set to the position (0, 0) in the XY coordinate system. The position in this case is referred to as a bed origin position.

Next, the bed 200 is moved toward one side in the X-axis direction, and the sensing point of the nozzle end alignment sensor 250 is positioned under the nozzle of the first print module positioned at the position ($X_1$, 0).

Next, the first print module 400 is moved downward, and a Z value of the nozzle end of first print module 400 is calculated and measured from a descent distance. When the Z value of the nozzle end of the first print module 400 is referred to as a $Z_1$ value, the measured Z value, that is, the $Z_1$ value, of the nozzle end of the first print module 400 is input to the controller. Movement of the first print module 400 on the Z-axis is controlled on the basis of the input $Z_1$ value.

Next, the first print module 400 is positioned at the original position, the bed 200 is moved toward the other side in the X-axis direction to return to the bed origin position. The bed is further moved toward the other side from the bed origin position in the X-axis direction, and the sensing point of the nozzle end alignment sensor 250 is positioned at the position ($X_2$, 0) under the nozzle of the first syringe, which is disposed at a printing position, in the second print module 500. Before printing is performed, the first syringe is set to be positioned at the printing position of the second print module.

The first syringe holder is moved downward from a standby height to a printing start height, the second print module is moved downward, and a Z value of the nozzle end of the first syringe is calculated and measured from a descent distance. The Z value of the nozzle end of the first syringe is referred to as a $Z_{21}$ value, the measured Z value, that is, the $Z_{21}$ value, of the end nozzle of the first syringe is input to the controller. Movement of the first syringe of the second print module on the Z-axis is controlled on the basis of the input $Z_{21}$ value.

Next, the first syringe is moved upward, the rotary shaft is rotated to move the second syringe to the printing position, and a Z value of the nozzle end of the second syringe is measured through the same method. When the Z value of the nozzle end of the second syringe is referred to as a $Z_{22}$ value, the Z value, that is, the $Z_{22}$ value, of the nozzle end of the second syringe is input to the controller. Movement of the second syringe of the second print module on the Z-axis is controlled on the basis of the input $Z_{22}$ value.

Next, a Z value of the nozzle end of the third syringe, a Z value of the nozzle end of the fourth syringe, and a Z value of the nozzle end of the fifth syringe are measured through the same method, and a $Z_{23}$ value, a $Z_{24}$ value, and a $Z_{25}$ value are input to the controller.

As described above, the syringe of which the Z value of the nozzle end is measured first is designated as a first syringe, and the rotary shaft repeats forward rotation and reverse rotation within a rotation angle 180° in the clockwise direction and the counterclockwise direction to move the syringe holder to the printing position so as to measure the Z values of the nozzle ends of the syringes.

After the Z values of the nozzle ends of the syringes are measured, the first syringe returns to the printing position, and the bed 200 returns to the bed origin position. Next, the nozzle end alignment sensor 250 is removed.

Next, in the printing plate installation operation (S200), the printing plate 201 is installed on the bed 200.

The printing plate 201 is fixed at a preset position on the bed 200, the case door 12 and the chamber door 110 are closed and the interior of the printing chamber 100 is isolated from the outside.

Next, the sterilizing operation (S300) is performed. $H_2O_2$ gas is introduced into the printing chamber 100 through the sterilization gas inlet 162 and a sterilization process is performed, and after a plasma $H_2O_2$ sterilization process is performed, ventilation which exhausts the $H_2O_2$ gas to the outside is performed.

Next, the printing reference height correction operation (S400) is performed.

An operation in which the ultrasonic level sensor 710 installed in the center module 700 in the printing chamber scans the bottom surface of the printing plate 201 to measure an actual height of the bottom surface of the printing plate 201 is performed. In addition, the controller 900 performs comparing a profile of the actual height of bottom surface of the printing plate 201 and a preset printing reference height to calculate a leveling offset value. Next, an operation in which the calculated offset value is applied to correct the preset printing reference height is performed. Since the printing reference height correction operation is performed, the printing may be performed on the basis of the corrected printing reference height.

Next, the printing operation (S500) in which printing is performed by the first print module and the second print module is performed.

The bed 200 is moved under the first print module 400, and the nozzle of the first print module is moved along the preset moving passage on the printing plate 201 to print a structure such as a scaffold, a pharmaceutical structure, and a frame structure.

Next, the bed 200 is moved under the second print module 500, the selected syringe of the second print module 500 is moved to the printing position on the printing plate 201. When the selected syringe in the second print module 500 is moved to the printing position, the NFC reader 750 reads the NFC tag 610 of the syringe. The controller 900 drives the heating element and the cooling part provided in the syringe holder 540 to adjust an output temperature according to the read output conditions. Next, printing is performed according to the output conditions such as a printing speed and an air pressure recorded on the NFC tag 610 of the syringe 600. The printing is performed at the printing position in a state in which the syringe is moved downward from the standby height to the printing start height, and the bio-ink in the syringe is output through an air dispensing method due to an air pressure provided through the air tube.

In a case in which a specific layer printed while the printing operation is performed needs to be cured, after the corresponding layer is printed, the bed 200 is moved to the bed origin position, and the printout is exposed to UV light provided by the UV curing device 720 so that the printout is cured.

According to the embodiment of the present invention, after the printing is completed, $CO_2$ incubation may be performed in a non-stop manner.

The $CO_2$ incubation operation (S600) is performed by adjusting an internal carbon dioxide concentration of the printing chamber using $CO_2$ gas introduced through the incubation gas inlet and a temperature and a humidity using the temperature controller and the humidity controller.

While the printing operation (S500) and the $CO_2$ incubation operation (S600) are performed, cell formation observation and the like may be performed, moving images may be captured, and recording may be performed using the high magnification camera module 730 installed in the center module 700 as necessary.

Next, when final completion of the printing is determined, the operation of the printer is stopped, the case door and the chamber door are opened, and the printout is unloaded.

The invention claimed is:

1. A three-dimensional (3D) bioprinter comprising:
   a case;
   a printing chamber provided in the case, surrounded by wall surfaces so that an interior thereof is isolatable from the outside, and provided with a chamber door;
   a moving unit including a horizontal moving unit installed in a space under a bottom surface of the printing chamber and a vertical moving unit installed outside a side surface of the printing chamber;
   a bed supported by the horizontal moving unit to be disposed above a bottom surface opening and installed to be movable in X-axis and Y-axis directions, wherein the bottom surface opening is formed in the bottom surface of the printing chamber;
   a first bellows which covers a space between the bed and an inner circumferential surface of the bottom surface opening to isolate the interior of the printing chamber from the space under the bottom surface of the printing chamber and is deformed according to movement of the bed to allow the bed to be moved in the X-axis and Y-axis directions;
   a first print module provided in the printing chamber and installed to be vertically movable by the vertical moving unit in a Z-axis direction;
   a second print module provided at one side of the first print module in the printing chamber and installed to be vertically movable by the vertical moving unit in the Z-axis direction;
   a controller configured to control operation of the moving unit, operation of the first print module, and operation of the second print module;
   a hollow cylindrical part fixed to an upper surface opening of the printing chamber and having open upper and lower ends; and
   a packing plate which is installed in the cylindrical part and divides the cylindrical part into an upper section and a lower section isolated from each other,
   wherein the second print module is disposed under the packing plate.

2. The 3D bioprinter of claim 1, further comprising:
   a hollow tube which extends through a side surface opening formed in the printing chamber, is supported by the vertical moving unit, and is installed to be movable in the Z-axis direction; and
   a second bellows which covers a space between an outer circumferential surface of the hollow tube and an inner circumferential surface of the side surface opening to isolate the interior of the printing chamber from an outside of the side surface of the printing chamber and is deformed according to movement of the hollow tube to allow the hollow tube to be moved in Z-axis direction, wherein the first print module is connected to the hollow tube to be vertically moved with the hollow tube.

3. The 3D bioprinter of claim 2, further comprising a blocking plate which closes an end portion of the hollow tube,
wherein the first print module is installed on the blocking plate to be replaceable, and
a connector is formed on the hollow tube or the blocking plate.

4. The 3D bioprinter of claim 1, further comprising a temperature controller configured to adjust an internal temperature of the printing chamber,
wherein the temperature controller includes a water jacket formed outside the wall surface of the printing chamber and configured to accommodate water and a heater configured to provide heat into the water jacket.

5. The 3D bioprinter of claim 1, further comprising:
an air circulator configured to circulate air in the printing chamber; and
a humidity controller configured to adjust an internal humidity of the printing chamber,
wherein the air circulator includes an inlet through which air is introduced from the printing chamber, an air duct through which the air introduced through the inlet moves, an outlet formed as an opening provided in the side surface of the printing chamber, and a filter configured to filter the circulating air, and
the humidity controller includes a tray configured to accommodate water to be provided to a side of the outlet.

6. The 3D bioprinter of claim 5, wherein the humidity controller includes a heating element disposed under the bottom surface of the printing chamber and configured to heat the water contained in the tray.

7. The 3D bioprinter of claim 5, further comprising a temperature controller including a water jacket formed outside the wall surface of the printing chamber and configured to accommodate water and a heater configured to provide heat into the water jacket,
wherein the air duct extends through an interior of the water jacket.

8. The 3D bioprinter of claim 1, wherein:
a sterilization gas inlet and a sterilization gas outlet are formed in the printing chamber;
the printing chamber is connected to a sterilization gas generator disposed outside the printing chamber through the sterilization gas inlet to allow sterilization in the printing chamber; and
a sterilization gas is exhaustible through the sterilization gas outlet.

9. The 3D bioprinter of claim 1, wherein:
an incubation gas inlet and an incubation gas outlet are formed in the printing chamber; and
the printing chamber is connected to a $CO_2$ tank through the incubation gas inlet so that an internal $CO_2$ concentration thereof is controllable.

10. The 3D bioprinter of claim 1, wherein a center module, in which an ultrasonic level sensor configured to measure an actual height profile of a bottom surface of a printing plate installed on the bed is installed, is provided between the first print module and the second print module.

11. The 3D bioprinter of claim 1, wherein a center module, in which a high definition camera configured to function as a microscope configured to observe a printout on a printing plate installed on the bed is installed, is provided between the first print module and the second print module.

12. The 3D bioprinter of claim 1, wherein the second print module includes a syringe holder in which a syringe filled with a fluid-state biomaterial is installed,
wherein the syringe holder includes a heating element and a cooling block configured to adjust a temperature of the syringe.

13. The 3D bioprinter of claim 12, wherein:
a reader configured to read information of a tag attached to the syringe installed in the syringe holder is provided in the printing chamber; and
the controller is configured to control the temperature and an output of the syringe according to the information read by the reader.

14. The 3D bioprinter of claim 1, wherein the second print module includes a plurality of syringe holders disposed in a circumferential direction, wherein syringes filled with fluid-state biomaterials are each installed in one of the plurality of syringe holders, and the 3D bioprinter further comprises:
a rotary shaft of which one end is fixed to the packing plate and which extends upward;
a rotary shaft support part which rotatably supports the rotary shaft;
a support of which one end is fixed to the rotary shaft support part and the other end is fixed to the vertical moving unit to allow the rotary shaft to move vertically; and
a rotary shaft driving motor configured to rotate the rotary shaft.

15. The 3D bioprinter of claim 14, wherein:
the rotary shaft driving motor of the support includes an encoder motor;
a potentiometer is installed on the support;
a pulley, which is positioned on an upper surface of the support, is included in each of an end portion of the rotary shaft, an end portion of the potentiometer, and an end portion of the encoder motor; and
timing belts are installed between the pulley of the end portion of the rotary shaft and the pully of the end portion of the potentiometer and between the pully of the end portion of the potentiometer and the pully of the end portion of the encoder motor.

16. The 3D bioprinter of claim 15, further comprising:
a syringe holder moving shaft of which a lower end is fixed to the syringe holder and which passes through the packing plate and extends upward;
a fixed guide which is fixed to an upper surface of the packing plate and through which the syringe holder moving shaft passes;
a moving guide fixed to an upper portion of the syringe holder moving shaft and configured to move the syringe holder moving shaft from a standby height to a printing start height;
a spring configured to move the moving guide upward when an external force, by which the moving guide is moved downward, is not applied to the moving guide;
a cam configured to rotate to push the moving guide of the syringe holder, which is moved to a printing position, downward to the printing start height; and
a cam driving motor configured to drive the cam.

17. The 3D bioprinter of claim 16, further comprising:
a magnet attached to the moving guide of each of the syringe holders; and
a magnetoresistive (MR) sensor configured to detect the magnet attached to the moving guide of the syringe holder to detect whether the syringe holder rotates and moves to the printing position.

\* \* \* \* \*